United States Patent [19]

Zvenyatsky et al.

[11] Patent Number: 5,626,609

[45] Date of Patent: *May 6, 1997

[54] ENDOSCOPIC SURGICAL INSTRUMENT

[75] Inventors: Boris Zvenyatsky, Bronx, N.Y.; Ernie Aranyi, Easton, Conn.

[73] Assignee: United States Surgical Corporation, Norwalk, Conn.

[*] Notice: The portion of the term of this patent subsequent to Feb. 15, 2014, has been disclaimed.

[21] Appl. No.: 357,536

[22] Filed: Dec. 16, 1994

Related U.S. Application Data

[63] Continuation of Ser. No. 934,728, Aug. 24, 1992, abandoned, which is a continuation-in-part of Ser. No. 780,273, Oct. 18, 1991, abandoned, which is a continuation-in-part of Ser. No. 593,670, Oct. 5, 1990, abandoned.

[51] Int. Cl.⁶ .................................................. A61B 17/00
[52] U.S. Cl. ........................ 606/208; 606/206; 606/207
[58] Field of Search ............................... 606/205–211; 128/751, 752

[56] References Cited

U.S. PATENT DOCUMENTS

| | | |
|---|---|---|
| D. 246,190 | 10/1977 | Hodge . |
| 459,818 | 9/1891 | Pearson et al. . |
| 487,068 | 11/1892 | Drinkwater . |
| 825,121 | 7/1906 | Frentzen et al. . |
| 943,263 | 12/1909 | Moraweck . |
| 1,452,373 | 4/1923 | Gomez . |
| 1,513,367 | 10/1924 | Brix . |
| 1,659,112 | 2/1928 | Littlejohn . |
| 1,749,261 | 3/1930 | Reisler . |
| 1,754,806 | 4/1930 | Stevenson . |
| 1,816,952 | 8/1931 | Bergman . |
| 1,855,546 | 4/1932 | File . |
| 2,002,594 | 5/1935 | Wappler et al. . |
| 2,034,785 | 3/1936 | Wappler . |
| 2,070,670 | 2/1937 | Marshall . |
| 2,305,156 | 12/1942 | Grubel . |
| 2,397,823 | 4/1946 | Walter . |
| 2,601,513 | 6/1952 | Gladstone . |
| 2,618,268 | 11/1952 | English . |
| 2,642,871 | 6/1953 | Thuerig . |
| 2,668,538 | 2/1954 | Baker . |
| 2,723,666 | 11/1955 | Greenberg . |
| 2,790,437 | 4/1957 | Moore . |
| 2,796,065 | 6/1957 | Kapp . |
| 2,898,915 | 8/1959 | Kammer . |

(List continued on next page.)

FOREIGN PATENT DOCUMENTS

| | | |
|---|---|---|
| 0176351 | 4/1986 | European Pat. Off. . |
| 0380874 | 8/1990 | European Pat. Off. . |

(List continued on next page.)

OTHER PUBLICATIONS

Sklar Products, "Surgical Instruments: Suction and Pressure Apparatus," 1973, 18th ed., pp. 67 and 100.

Solos Endoscopy Brochure, "Instrument Set: Advanced Laparoscopic Surgical Devices" 2 pages.

(List continued on next page.)

*Primary Examiner*—David M. Shay

[57] ABSTRACT

An endoscopic surgical instrument having a handle assembly, a body portion, and a tool mechanism in which a pivoting handle pivots about a stationary handle to open and close the tool mechanism. The instrument includes a rotatable body portion, in which a rotation knob is provided on the instrument at the stationary handle so that the user may rotate the body portion, and consequently the tool mechanism, using a single hand. Furthermore, an electrocautery connection is provided which is positioned out of the line of sight of the surgeon, so that the surgeon may have an unobstructed view to the surgical site. The pivoting handle is provided with a rotatable connection point for connecting the slidable rod member to essentially eliminate radial deflection of the rod within the outer tube during opening and closing of the handles. The tool mechanism may include grasping jaws having rounded, interdigitating teeth for grasping and securely holding tissue or organs for removal through a cannula.

11 Claims, 21 Drawing Sheets

U.S. PATENT DOCUMENTS

| | | |
|---|---|---|
| 2,898,916 | 8/1959 | Kammer . |
| 3,101,715 | 8/1963 | Glassman . |
| 3,209,753 | 10/1965 | Hawkins et al. . |
| 3,404,677 | 10/1968 | Springer . |
| 3,426,757 | 2/1969 | Shannon et al. . |
| 3,446,211 | 5/1969 | Markham ................................. 606/207 |
| 3,503,398 | 3/1970 | Fogarty et al. . |
| 3,506,012 | 4/1970 | Brown . |
| 3,515,139 | 6/1970 | Mallina . |
| 3,557,792 | 1/1971 | Rubin . |
| 3,585,985 | 6/1971 | Gould . |
| 3,646,939 | 3/1972 | Sklar . |
| 3,746,002 | 7/1973 | Haller . |
| 3,807,406 | 4/1974 | Rafferty et al. . |
| 3,840,003 | 10/1974 | Komiya . |
| 3,895,636 | 7/1975 | Schmidt . |
| 3,921,641 | 11/1975 | Hulka . |
| 3,964,468 | 6/1976 | Schulz . |
| 4,005,714 | 2/1977 | Hiltebrandt . |
| 4,038,987 | 8/1977 | Komiya . |
| 4,043,343 | 8/1977 | Williams . |
| 4,049,002 | 9/1977 | Kletschka et al. . |
| 4,054,143 | 10/1977 | Bauer . |
| 4,064,881 | 12/1977 | Meredith . |
| 4,128,099 | 12/1978 | Bauer . |
| 4,169,476 | 10/1979 | Hiltebrandt . |
| 4,201,213 | 5/1980 | Townsend . |
| 4,243,047 | 1/1981 | Olsen . |
| 4,282,884 | 8/1981 | Boebel . |
| 4,345,589 | 8/1982 | Hiltebrandt . |
| 4,369,788 | 1/1983 | Goald . |
| 4,433,687 | 2/1984 | Burke et al. . |
| 4,512,343 | 4/1985 | Falk et al. . |
| 4,522,206 | 6/1985 | Whipple et al. ................. 128/752 |
| 4,569,131 | 2/1986 | Falk et al. . |
| 4,572,185 | 2/1986 | Rich . |
| 4,574,804 | 3/1986 | Kurwa . |
| 4,590,936 | 5/1986 | Straub et al. . |
| 4,643,190 | 2/1987 | Heimberger . |
| 4,646,751 | 3/1987 | Maslanka . |
| 4,669,471 | 6/1987 | Hayashi . |
| 4,674,501 | 6/1987 | Greenberg . |
| 4,712,545 | 12/1987 | Honkanen . |
| 4,721,116 | 1/1988 | Schintgen et al. . |
| 4,759,364 | 7/1988 | Boebel . |
| 4,763,668 | 8/1988 | Macek et al. . |
| 4,815,460 | 3/1989 | Porat et al. . |
| 4,819,633 | 4/1989 | Bauer et al. . |
| 4,872,456 | 10/1989 | Hasson . |
| 4,887,612 | 12/1989 | Esser et al. . |
| 4,896,678 | 1/1990 | Ogawa . |
| 4,898,157 | 2/1990 | Messroghli et al. . |
| 4,919,152 | 4/1990 | Ger . |
| 4,976,723 | 12/1990 | Schad . |
| 4,986,825 | 1/1991 | Bays et al. . |
| 4,994,024 | 2/1991 | Falk . |
| 4,994,079 | 2/1991 | Genese et al. . |
| 5,133,724 | 7/1992 | Wilson, Jr. et al. . |
| 5,147,378 | 9/1992 | Markham . |
| 5,171,256 | 12/1992 | Smith et al. . |
| 5,171,258 | 12/1992 | Bales et al. . |
| 5,176,699 | 1/1993 | Markham . |
| 5,258,004 | 11/1993 | Bales et al. . |

FOREIGN PATENT DOCUMENTS

| | | |
|---|---|---|
| 0484671 | 5/1992 | European Pat. Off. . |
| 0543107 | 5/1993 | European Pat. Off. . |
| 840884 | 6/1952 | Germany . |
| 1065565 | 9/1959 | Germany . |
| 1566060 | 6/1970 | Germany . |
| 3013836 | 10/1981 | Germany . |
| 3802651 | 3/1989 | Germany . |
| 8900376 | 4/1989 | Germany . |
| 8903782 | 10/1989 | Germany . |
| 9106506 | 9/1991 | Germany . |
| 9109097 | 10/1991 | Germany . |
| 121537 | 6/1958 | U.S.S.R. . |
| 4688 | of 1893 | United Kingdom . |
| 2086792 | 5/1982 | United Kingdom . |

OTHER PUBLICATIONS

Catalog for Karl Storz Endoscope Operating Instruments 4 pages.
Padgett Instruments Bulletin 1 page Jun. 1976.
Elmed Surgical Instruments Catalog 8 pages.
Karl Storz Endoscope Operating Instruments Catalog 4 pages.
Richard Wolf Medical Instruments Corp. Catalog 5 pages.

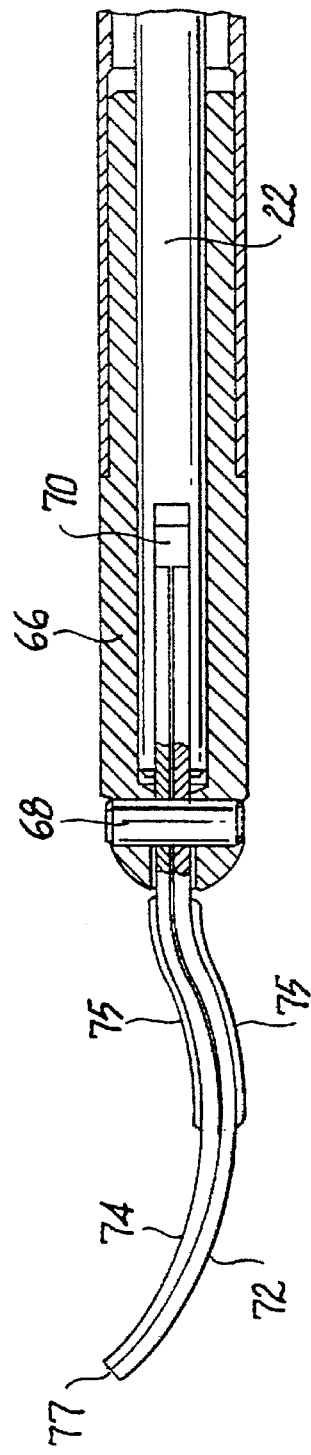
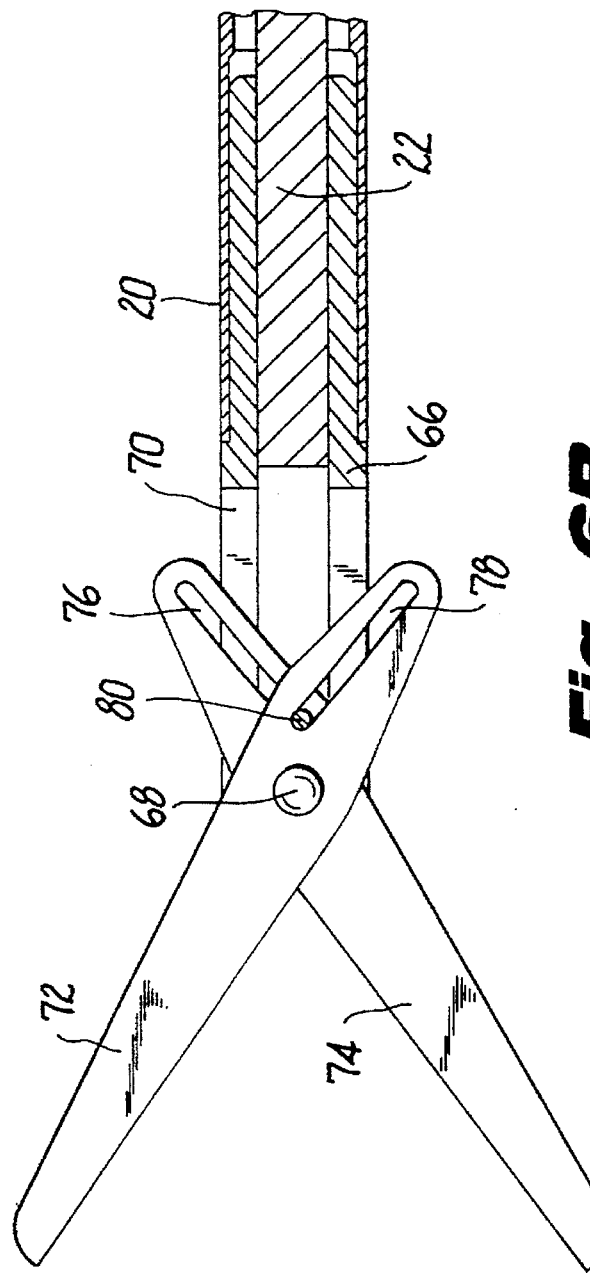
Fig. 6A
Fig. 6B

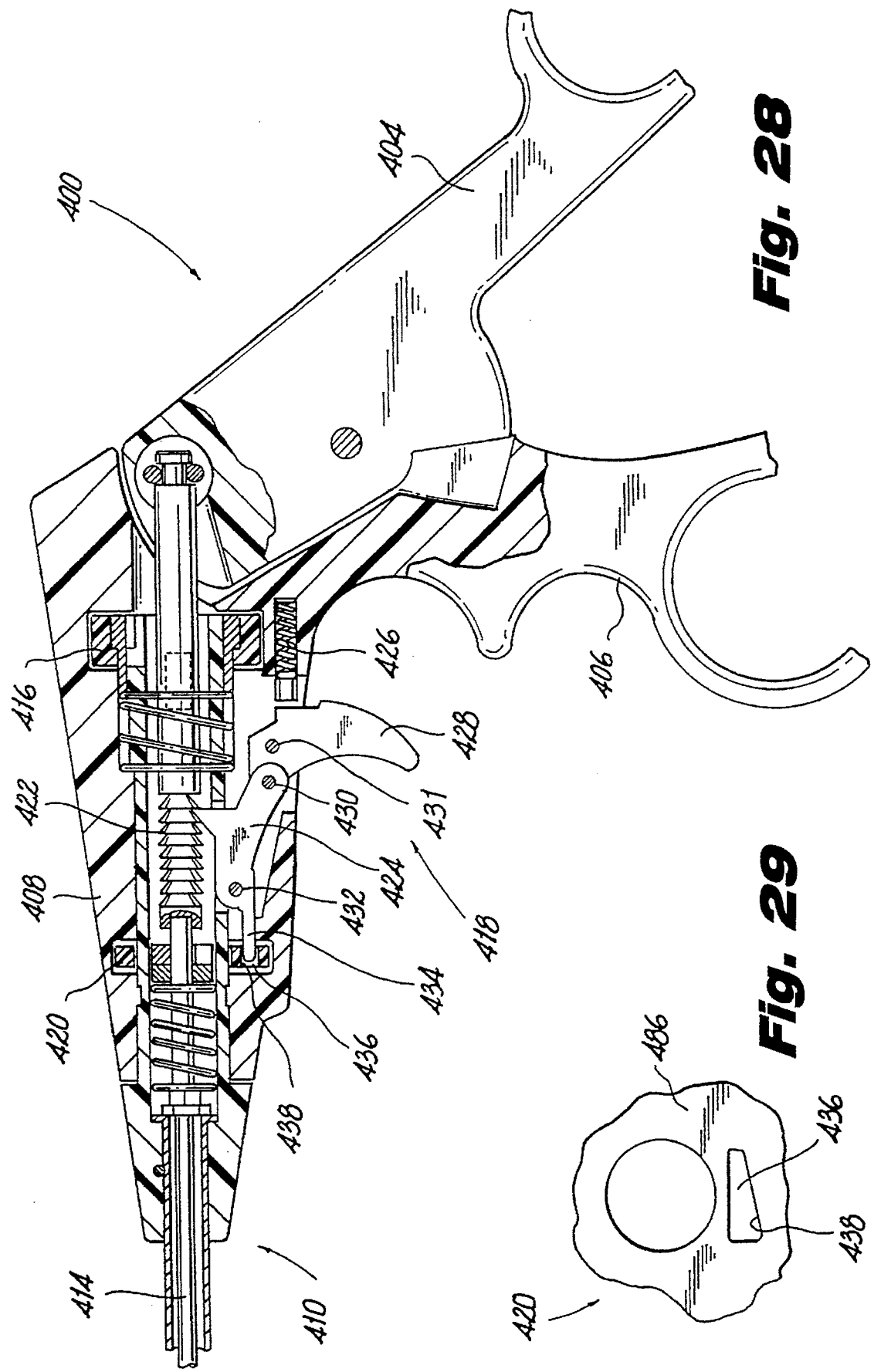

ENDOSCOPIC SURGICAL INSTRUMENT

CROSS-REFERENCE TO RELATED APPLICATIONS

This is a continuation of application Ser. No. 07/934,728 filed on Aug. 24, 1992 now abandoned which is a continuation-in-part of U.S. Ser. No. 780,273 filed Oct. 18, 1991, now abandoned, which is a continuation-in-part of U.S. Ser. No. 593,670, filed Oct. 5, 1990 now abandoned.

BACKGROUND OF THE INVENTION

1. Field of the Invention

The present invention relates to endoscopic surgical instruments, and more particularly relates to an endoscopic instrument having reciprocating jaw members which pivot in response to the opening and closing of a handle member, where the movement of the handles is translated through an elongated tubular body member to open and close the jaw mechanism.

The present invention further provides a device in which the jaw mechanism may comprise cutting scissor blades, a gripping device for holding tissue during surgery, and a grasping device for holding surgical needles and the like. The device of the present invention may be provided with a rotatable tubular body for selectively positioning the angle at which the jaw mechanism operates, and provision is also made for the use of electrocautery capabilities to provide for cauterization at the surgical site.

2. Discussion of the Prior Art

In the prior art, various endoscopic surgical instruments are disclosed which utilize generally complex mechanisms for opening and closing handle members and jaw members to facilitate use of the device at a surgical site. Many devices provide an intricate construction in which a linkage mechanism for opening and closing the jaws requires numerous moving parts, while a sliding arrangement is provided between two extended rod members which activates the linkage mechanism in response to movement of the handle members. In addition, pivoting of the handle members in many cases causes an unwanted radial torquing force on the rod which requires additional space to be provided in the handle members to accommodate the radial movement of the rod.

Endoscopic devices presently in use include many devices having an interchangeable shaft assembly and jaw mechanism in which a common handle may be used with a series of instruments. However, these devices suffer disadvantages in that the connecting mechanism oftentimes obstructs the view of the surgeon, and the integrity of the device is decreased due to loosening of the connection. These disadvantages are critical due to the fact that an endoscopic surgical procedure requires precision instruments with tolerances that are carefully monitored. As the connections wear, precision is sacrificed, and the usefulness of the tool is diminished.

Greenberg, U.S. Pat. No. 4,674,501 discloses a surgical instrument having a pair of reciprocating shafts which are provided with a rotational indexing knob in which the shafts are allowed to rotate to position a cutting tool at a specific angle to the handles. The shafts slide on top of each other in response to opening and closing of the handle members to open and close the jaw members of the cutting instrument. The housing is secured to a stationary handle, such that the shaft assembly rotates with the indexing knob. One shaft is secured in a ball and socket joint to a movable handle which facilitates the sliding arrangement of the movable shaft over a stationary shaft. The handle assembly is disengagable from the housing by means of a screw, and the ball joint slides out of the socket to remove the handles. This type of device is subject to the disadvantage disclosed above, in which the integrity of the device is compromised due to the number of moving parts, as well as to the fact that the ball and socket joint is an inherently loose connection which will deteriorate during continued use.

Ger, U.S. Pat. No. 4,919,152, discloses a clip applying device having a stationary handle and a pivoting handle to which an elongated shaft arrangement is attached. At the end of the shaft is a pair of reciprocating jaw members which are operated in response to pivoting movement of the handles. An inner shaft member is attached to the pivoting handle, the shaft member passing through an outer tube member which is attached to the stationary handle. As the rod member passes through the stationary handle, as well as through the outer tube at the location it is attached to the stationary handle, radial movement of the rod within the outer tube must be accounted for since the rod is attached to the stationary handle at a non-movable point. In relation to this, the bushing member is necessary inside the stationary handle to accommodate the radial play in the rod member during opening and closing of the handles.

Straub et al., U.S. Pat. No. 4,590,936, discloses a microsurgical instrument having a complex gear mechanism for translating movement of the handles to an opening and closing movement of the jaw members. A helical slot is provided in a shaft member which allows a pin to move through the slot to move the jaw members. Furthermore, a ball and socket joint is provided in the movable handle to connect the movable handle to the inner rod.

Bauer, U.S. Pat. No. 4,128,099, discloses a forceps device having an attachment for cauterization which conducts current through the outer tube to the jaw mechanism. A complex insulation system is provided to insulate the handle from the shaft, as well as to insulate the shaft itself. This device suffers the disadvantage that in order to insulate the handle, the rod member is secured to an insulating bushing, and a second rod is provided to the bushing to connect to the handle members. Furthermore, the connection point for the electrical connector is positioned in an area which will obstruct the view of the surgeon as he looks down the device to a surgical site.

The novel endoscopic surgical instrument pursuant to the present invention obviates the disadvantages encountered in the prior art and provides a precise instrument which is easy to manufacture and efficient to use, which eliminates many of the moving parts required by prior art devices. The instrument of the present invention incorporates many features which are of use to the surgeon during an operation, while it maintains a lightweight construction in an easy to handle device in which all the features may be operated with one hand. Furthermore, the features are so positioned so as to provide a maximum line of sight for the surgeon without obstructing the view to the surgical site.

SUMMARY OF THE INVENTION

The present invention provides a novel endoscopic surgical device which incorporates many features necessary for an endoscopic surgical procedure, and provides a lightweight and easy to use device which may be operated with one hand. The device is simple to manufacture, and may incorporate any one of a series of jaw mechanisms for various surgical procedures. The device is a high precision instrument in which many moving parts normally associated with such a device are eliminated, thus reducing instances of mechanical failure requiring expensive repair or ultimate destruction of the instrument.

The endoscopic surgical instrument of the present invention essentially consists of a handle assembly, an elongated body assembly, and a tool mechanism attached at a distal end of the body assembly remote from the handle assembly. The handle assembly includes a stationary handle and pivoting handle, whereby the body assembly is attached to the stationary handle assembly and extends therefrom. The body assembly consists of an outer tubular member and an inner rod member which coaxially passes within the outer tubular member. The rod member is attached to the pivoting handle, while the tube member is secured in a conventional manner to the stationary handle. Preferably, the outer tube is provided with a detent which cooperates with a boss on the interior of the stationary handle to lock the outer tube in place. As the pivoting handle moves, the rod member slidably reciprocates within the outer tube member.

Attached to a distal end of the body assembly is provided the tool mechanism which opens and closes in response to movement of the pivoting handle in relation to the stationary handle. The tool mechanism may comprise a pair of jaw members wherein one or both jaw members open and close to perform various endoscopic surgical procedures. The jaw mechanism includes, but is not limited to, a scissor device, a dissecting device, a tissue gripping device, a grasping device and the like. In a preferred embodiment, the jaw mechanism includes two elongated grasping jaws which include a plurality of teeth adapted to mesh and directly interfit.

In one embodiment the jaw mechanism is secured to the outer tubular member by means of a transverse post member which serves as a common pivot point about which both jaw members pivot. Each jaw member is provided with a camming portion which extends away from the pivot point, and consists of a cam slot which extends from the pivot point into the outer tube. The upper jaw is generally provided with a pair of spaced apart projections, each provided with a cam slot which transversely overlap each other. The lower jaw is also provided with a pair of extensions which are spaced apart a distance which is less than the space between the projections of the upper jaw member so that the lower projections pass between the upper projections. The lower projections are also provided with transverse overlapping slots which are positioned at an angle to the upper cam slots. The jaw mechanism is secured to the outer rod through the common pivot point.

The inner rod member is provided with a bearing surface, which typically comprises a post member which passes through and is engaged within the cam slots of both jaw members. As the pivoting handle is moved, the rod slides through the outer tube and causes the post member to bear on the camming slots to pivot the jaw members about the common pivot point to open the Jaw members. Since the cam slots are at an angle to each other, movement of the post member through the slots pivots both jaw members as the post rides through the slots. As the rod reciprocates, the jaw mechanism opens and closes.

In order to prevent excessive forces from being applied to the jaw mechanism, the pivoting handle is provided with a pair of stop members which are positioned proximate the pivot point which secures the pivoting handle to the stationary handle, and about which the pivoting handle moves. The upper, or proximal stop member abuts a boss within the stationary handle to prevent the jaw mechanism from opening too wide, while a distal, or lower stop member abuts the stationary handle to prevent excessive forces from being applied to the jaw mechanism during closing. Accordingly, the application of force to the jaw mechanism may be regulated during design and manufacture by the interengagement of the stop members on the pivoting handle with the bosses on the stationary handle.

A novel feature of the present invention is the provision of a second pivot point on the pivoting handle, to which the inner rod member is attached. As the handle pivots, the second pivot point rotates to allow the inner rod to move longitudinally in the outer tube with minimal radial deflection. This is an important feature of the present invention in that it reduces the radial wear on the inner rod and prevents weakening of the structure during long term use. In addition, it allows for a reduction of the required internal spacing between the outer tube and the inner rod to result in a more compact and streamlined instrument. Furthermore, unwanted torquing forces are eliminated at the pivot point thus minimizing the possibility of mechanical breakdown of the instrument at the connection between the pivoting handle and the movable inner rod.

The present invention may also feature a connection port to provide the device with electrocautery capabilities. In this embodiment of the invention, a connection port is provided, preferably on the stationary handle on the side of the longitudinal axis opposite the finger grip portion. The connection port is positioned at an angle to the longitudinal axis, which is preferably less than 30° and in a preferred embodiment is approximately 9° to the longitudinal axis, and extends in a direction away from the body assembly. In this way, the surgeon's line of sight is unobstructed and provides a clear view to the surgical site. The connection port allows for the connection of a suitable jack member to be inserted into the device. Electrical connection between the port and the outer tube is provided by a leaf spring member which extends from the port area to the outer tube. The outer tube is provided with electrical insulation, preferably heat shrink tubing, which extends a substantial portion of the length of the outer tube. In this embodiment, the handle is molded of plastic material to provide electrical insulation to the user.

It is also contemplated that the electrical port connection may be provided adjacent the finger grip of the stationary handle, so that the jack member extends downwardly away from the device to insure an unobstructed line of vision for the surgeon. In this case, a leaf spring member extends from the port through the stationary handle to the outer tube to complete the electrical connection.

A further feature of the present invention is the provision of a rotatable knob on the outer tubular member to allow the body assembly and the jaw mechanism to rotate to position the jaws at desired angles to the longitudinal axis during the surgical procedure. Preferably, the rotatable knob is secured to the outer tube and positioned in a slot which passes through the stationary handle, so that a surgeon may rotate the knob, and consequently the body assembly and jaw mechanism, through the use of his thumb while he is holding the stationary handle with his fingers. This frees the surgeon's other hand to simultaneously operate another instrument during surgery.

Preferably, the rotatable knob is secured to a bushing, which in turn is secured to the outer tube member. The bushing is provided with a polygonal cross-section, which corresponds to a boss member within the interior of the stationary handle. This allows for incremental rotation of the body assembly and jaw mechanism to desired angles to the longitudinal axis. Preferably, the bushing has a dodecahedral cross-section.

In the preferred embodiment, all the above features are incorporated into a single endoscopic surgical instrument, so that the instrument has electrocautery and rotational capabilities. However, the instrument may be constructed without one or more of the features while still providing a lightweight precision instrument.

Accordingly, it is an object of the present invention to provide an endoscopic surgical instrument in which all the features may be used by a surgeon with one hand.

It is another object of the present invention to provide a lightweight endoscopic surgical instrument which provides a clear line of sight for a surgeon during a surgical procedure.

It is a further object of the present invention to provide an endoscopic surgical instrument which prevents the application of excessive forces to the working tool mechanism to prevent damage to the instrument, whether the tool mechanism is being opened or closed.

It is yet a further object of the present invention to provide an endoscopic surgical instrument in which tolerances between the inner slidable rod member which operates the jaws and the outer tubular member which holds the jaw mechanism are such that there is little or no radial deflection of the rod during longitudinal movement through the tube.

It is still a further object of the present invention to provide an endoscopic surgical instrument having a handle assembly in which a first pivot point is provided for pivoting the movable handle about the stationary handle and a second pivot point is provided which connects the movable rod member to the pivoting handle which allows for rotation of the second pivot point to prevent radial deflection of the rod during longitudinal movement.

It is yet another object of the present invention to provide an endoscopic surgical instrument having electrocautery capabilities in which the connection port for an electrical jack member is out of the line of sight of the surgeon during use.

It is still a further object of the present invention to provide an endoscopic surgical instrument having a rotatable body member and jaw mechanism in which the rotation may be accomplished by the surgeon while using one hand.

It is a further object of the present invention to provide an endoscopic instrument particularly suited to grasp and securely hold a gallbladder.

It is yet another object of the present invention to provide an endoscopic instrument and a tool mechanism for use with that instrument which is particularly suited to grasp and securely hold lung tissue.

It is still another object of the present invention to provide an endoscopic surgical instrument having all the features above including a rotatable body assembly and jaw mechanism, electrocautery capabilities, and a rotatable pivot point for connecting the inner rod to the pivot handle to prevent radial deflection of the rod during longitudinal movement.

BRIEF DESCRIPTION OF THE DRAWINGS

The foregoing objects and other features of the invention will become more readily apparent and may be understood by referring to the following detailed description of an illustrative embodiment of the endoscopic surgical instrument, taken in conjunction with the accompanying drawings, in which:

FIG. 6A shows a top cutaway view of the tool mechanism of an endoscopic surgical instrument according to the present invention;

FIG. 6B illustrates a side cutaway view of the tool mechanism of FIG. 6A of an endoscopic surgical instrument according to the present invention;

FIG. 28 illustrates a side cut-away view of the device of FIG. 26; and

FIG. 29 illustrates a plan view of an embodiment of the actuation means for use with the ratchet mechanism shown in FIG. 28.

DETAILED DESCRIPTION OF THE PREFERRED EMBODIMENTS

Figure 1:
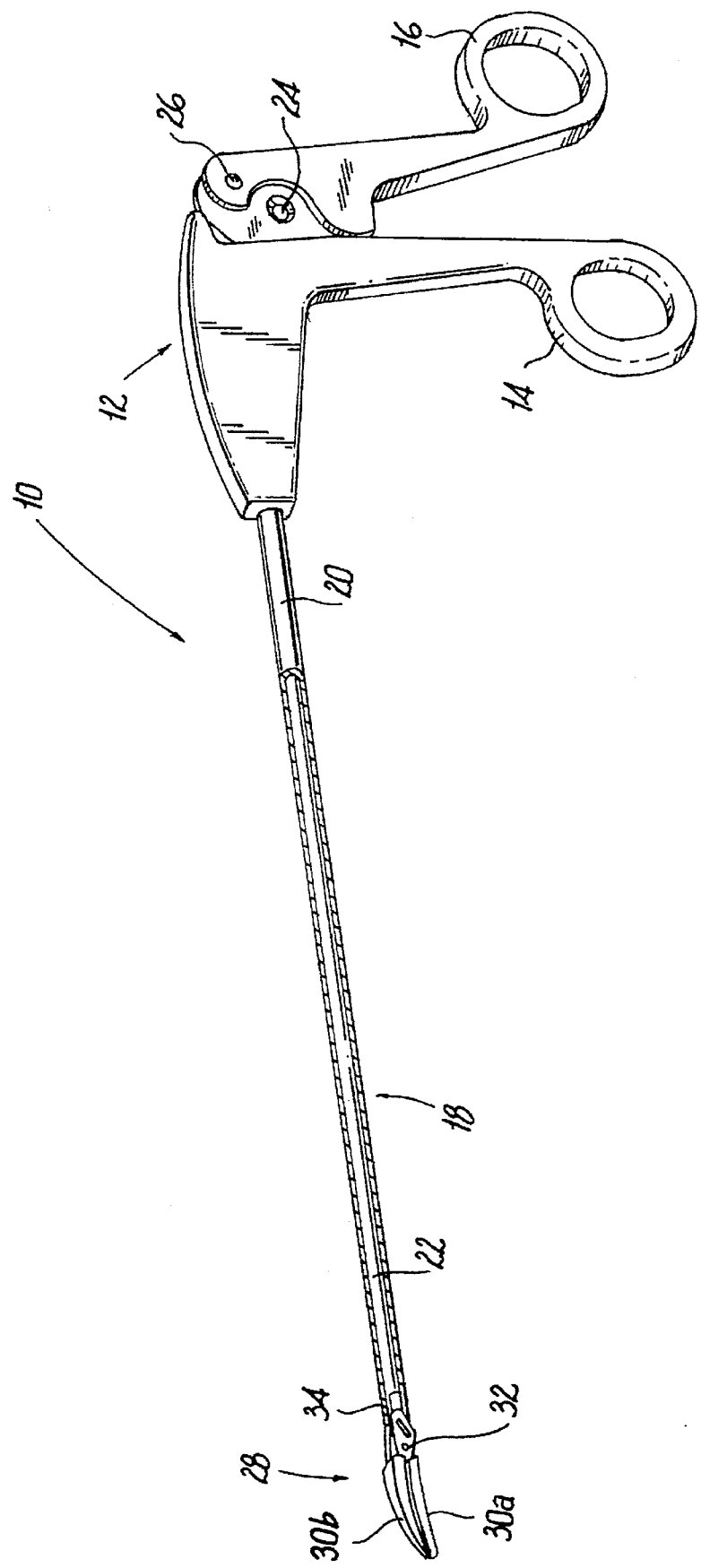
FIG. 1 illustrates a perspective view of an endoscopic surgical instrument in partial cutaway according to the present invention.

Referring now in specific detail to the drawings, in which like reference numbers identify similar or identical elements, FIG. 1 illustrates an embodiment of the endoscopic surgical instrument 10. In its simplest form, the device comprises a handle assembly 12 which consists of a stationary handle 14 and a pivoting handle 16. Extending from the handle assembly is a body portion 18 which comprises an outer tubular member 20 through which a slidable inner rod member 22 passes in coaxial relationship. The outer tube 20 is secured to the stationary handle 14, while the inner rod 22 is secured to pivoting handle 16 at rotatable connection point 26. Handle 16 pivots about pivot point 24 to move in relation to stationary handle 14.

Attached at a distal end of the body portion 18 is a tool mechanism 28, which essentially consists of a lower jaw member 30A and an upper jaw member 30B. The tool mechanism is connected to the body portion 18 at pivot point 32 and moves in a reciprocating manner about pivot point 32 through the provision of linkage mechanism 34. Linkage mechanism 34 will be described in greater detail below.

In use, as pivoting handle 16 pivots about pivot point 24 in relation to stationary handle 14, inner rod 22 reciprocatingly slides within outer tube 20 in response to the push or pull force at connection point 26. The function of connection point 26 will be described in greater detail below.

As rod 22 slides within tube 20, the linkage mechanism 34 is actuated to pivot jaw members 30A and 30B about pivot point 32 to open and close the members. Jaw members 30A and 30B may comprise scissors, dissecting jaws, or a grasping mechanism, or any other tool mechanism required for specific surgical procedures.

Figure 2:
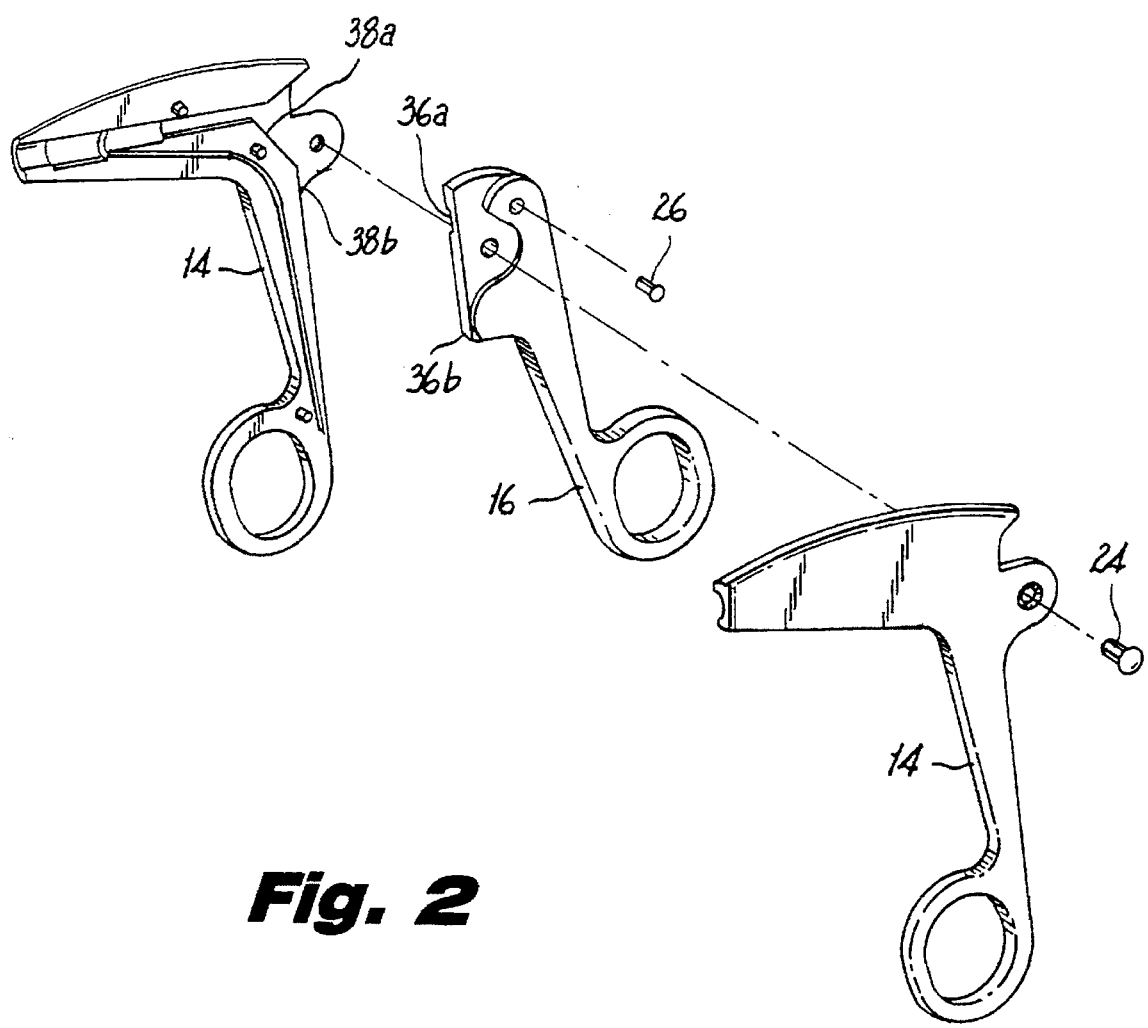
FIG. 2 illustrates an exploded perspective view of a handle of an endoscopic surgical instrument according to the present invention.

As best seen in FIG. 2, pivoting handle 16 is provided with a pair of stop members 36A and 36B which cooperate with boss members 38A and 38B, respectively, to limit the rotational movement about pivot point 24 of the pivoting handle 16. The stop members are positioned on opposite sides of pivot point 24 so that when pivoting handle 16 is moved away from stationary handle 14, proximal stop 36A contacts boss 38A to limit the actual rotation of handle 16. When handle 16 is moved towards handle 14, distal stop 36B contacts boss 38B to limit the rotation of handle 16 in that direction. The stop members are provided to prevent the application of excessive forces on the tool mechanism during opening and closing of the surgical instrument. In this manner, the possibility of damage or destruction of the tool mechanism is greatly reduced or eliminated.

Figure 3:
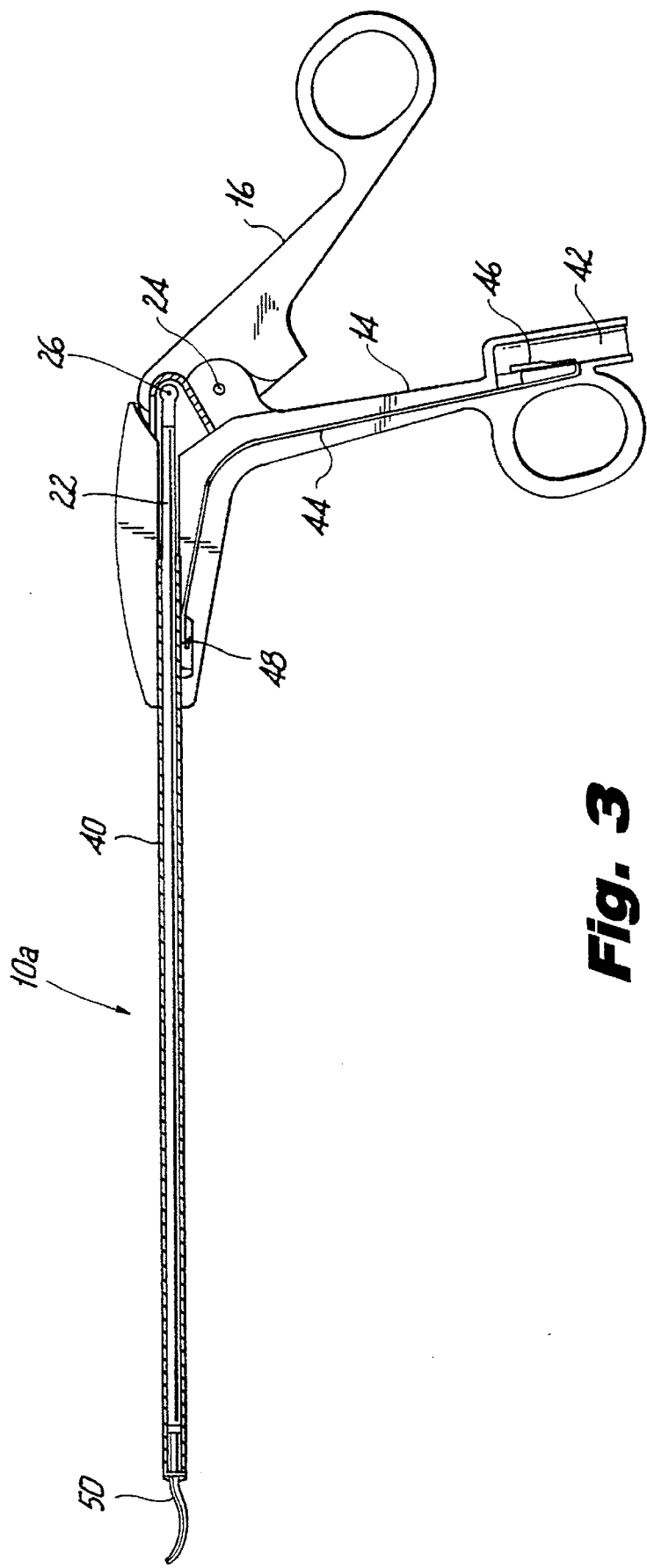
FIG. 3 illustrates a side cutaway view of an alternate embodiment of an endoscopic surgical instrument according to the present invention.

Turning now to FIG. 3, FIG. 3 illustrates a first alternate embodiment 10A of the endoscopic surgical instrument of the present invention. Instrument 10A is similar to instrument 10 except for the provision of an electrocautery connection to allow for cauterization of tissue at the surgical site during the surgical procedure. Stationary handle 14 is provided with a connection port 42 for the reception of an electrical jack member (not shown) for providing the necessary current to the tool. A leaf spring 44 electrically connects port 42 with outer tube member 20 which carries the electric current to the tool mechanism at the surgical site. The leaf spring is provided with a connection member 46 at the port 42 and a connection member 48 at the outer tube. The connection members essentially rely on the resiliency of the material which comprises the leaf spring, but of course may be any conventional electrical connection.

As the electrical charge is applied to the outer tube, it conducts along the outer tube to the tool mechanism, which in this instance is preferably a scissor device 50 or other tool mechanism such as cautery hooks, forceps, or the like. In order to protect the surgeon who is using the device from electrical shock, the handle is preferably constructed of a rigid plastic material which renders the device lightweight and electrically insulated.

In order to prevent electrical shock during use, an insulation member 40 is provided on outer tube 20, the insulation member preferably consisting of heat shrink tubing. Heat shrink tubing 40 passes into stationary handle 14 to prevent the possibility of electric shock.

While connection port 42 is shown as being attached to stationary handle 14 at the finger grip, it is also contemplated to position the connection port on top of the handle as shown and described below in relation to FIG. 5. The positioning of the connection port in the present invention is such so as to provide the surgeon with an unobstructed line of sight down body member 18 to view the surgical site at the tool mechanism 28.

Figure 4:
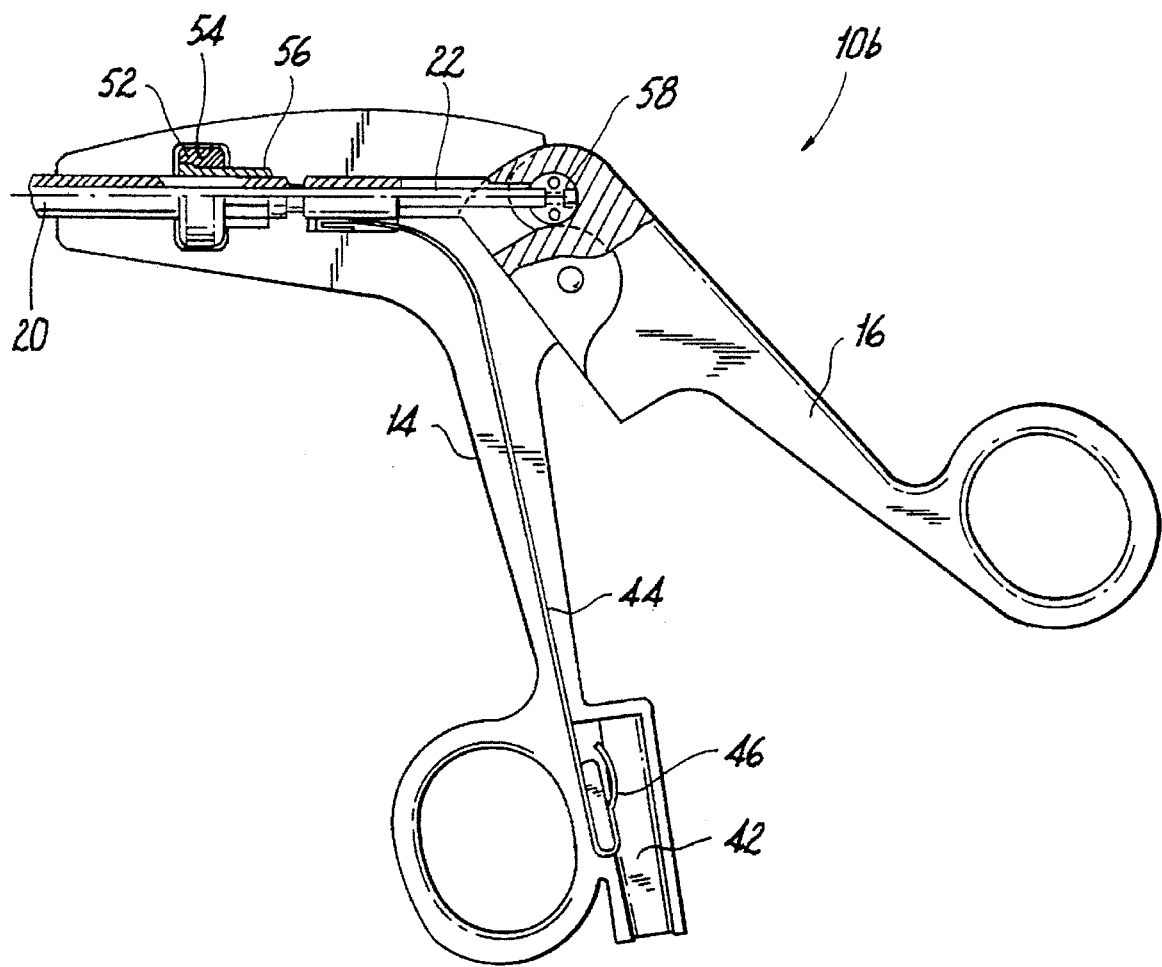
FIG. 4 illustrates a side cutaway view of a second alternate embodiment of an endoscopic surgical instrument according to the present invention.

FIG. 4 illustrates a preferred embodiment of the invention, in which the instrument 10B is provided with the electrocautery feature as well as having provisions for a rotatable body portion 18. As seen in FIG. 4, a slot 54 is provided in stationary handle member 14 which passes completely through the handle member. Positioned within the slot 54 is a rotatable knob 52 which is fixedly secured to outer tube 20 through the provision of a bushing member 56. The rotatable knob 52 and bushing member 56 will be described in greater detail below.

Also as best seen in FIG. 4, inner rod member 22 is connected to pivoting handle 16 through the provision of a rotational bushing 58. Bushing 58 pivots during movement of pivoting handle 16 so that as rod member 22 is reciprocated within tube 20, the bushing member 58 rotates to minimize or eliminate any radial movement of rod 22, to insure that rod 22 moves in a longitudinal direction only. This alleviates excessive torquing forces on rod member 22 as well as unwanted excessive forces at the connection point 26 to prevent damage to the handle or the inner rod member 22. Another feature provided by this rotational bushing member 58, is that by greatly reducing or eliminating radial movement of rod member 22, exact tolerances between the outer tube 20 and the inner rod member 22 may be maintained, so that less spacing is required and the instrument may be made in a smaller size than conventional endoscopic instruments. In addition, by greatly reducing or eliminating the radial deflection, the precision of the instrument is greatly enhanced. The features of rotational bushing member 58 will be described in greater detail below.

Figure 5:
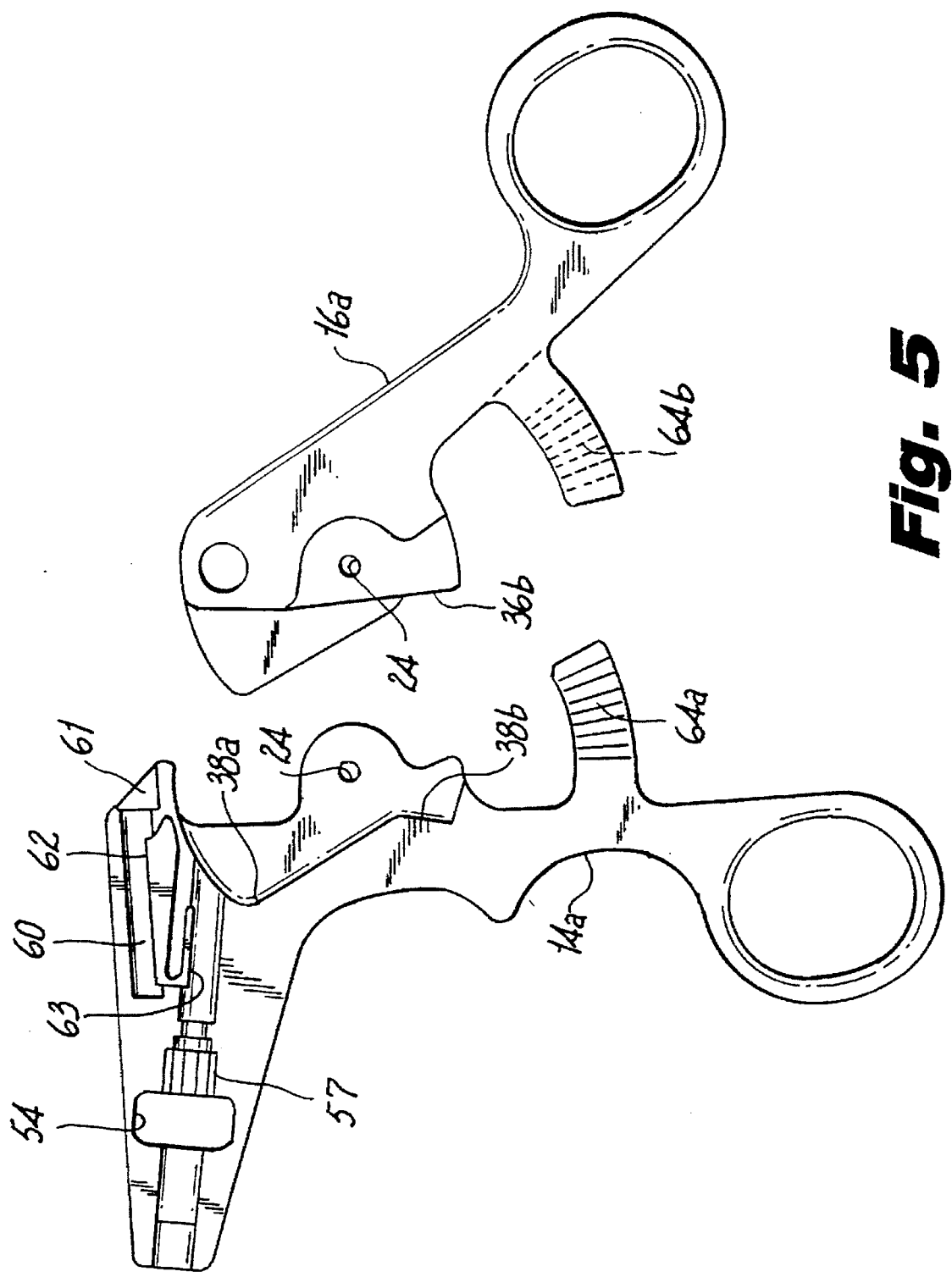
FIG. 5 illustrates a side cutaway view of a handle of a preferred embodiment of an endoscopic surgical instrument according to the present invention.

Turning now to FIG. 5, stationary handle 14A and pivoting handle 16A are illustrated having the provision of a locking mechanism 64A and 64B. FIG. 5 shows handle member 14A in a side cutaway view, and is the preferred embodiment of the present invention. As clearly seen in this view, handle member 14A and handle member 16A are attached at pivot point 24 so that during opening and closing of the handle assembly, proximal stop member 36A contacts boss 38A to limit rotation of pivoting handle 16A away from stationary handle 14A. When the handles are moved towards each other, stop member 36B contacts boss member 38B to limit rotation in that direction. Locking mechanism 64A and 64B may be utilized to position the handles at various locations during the opening and closing procedure, which of course allows for the application of various closing forces on the tool mechanism at the distal end of the instrument.

Handle 14A is provided with a slot 54 which accepts the rotatable knob 52. In addition, a polygonal shaped boss structure 57 is provided in the handle which will accept the corresponding polygonal shape of bushing member 56 when the instrument is constructed. The cooperation between structure 57 and bushing 56 allows for the incremental rotation of the body portion 18, and consequently the tool mechanism 28 to position the tool mechanism at various points along the rotational path. The number of faces presented by boss structure 57 is equivalent to the number of faces on the polygonal cross-section of bushing 56. Preferably, each structure has 12 faces.

In addition, FIG. 5 illustrates the preferred location of the electrical port 60, that being at the top of handle member 14A positioned at an angle to the longitudinal axis of the instrument formed by the body portion 18. Port 60 is preferably positioned at an angle of less than 30° to the longitudinal axis, and in its most optimal position, is positioned at 9° to the longitudinal axis. This affords the surgeon a clear line of sight down the longitudinal axis of the instrument to view the procedure at the surgical site. Port 60 accepts an electrical jack member through hole 61, and an electrical connection is made through the provision of a leaf spring member held in track 62 which connects the jack (not shown) with the outer tube member as seen at 63.

Figure 11A:
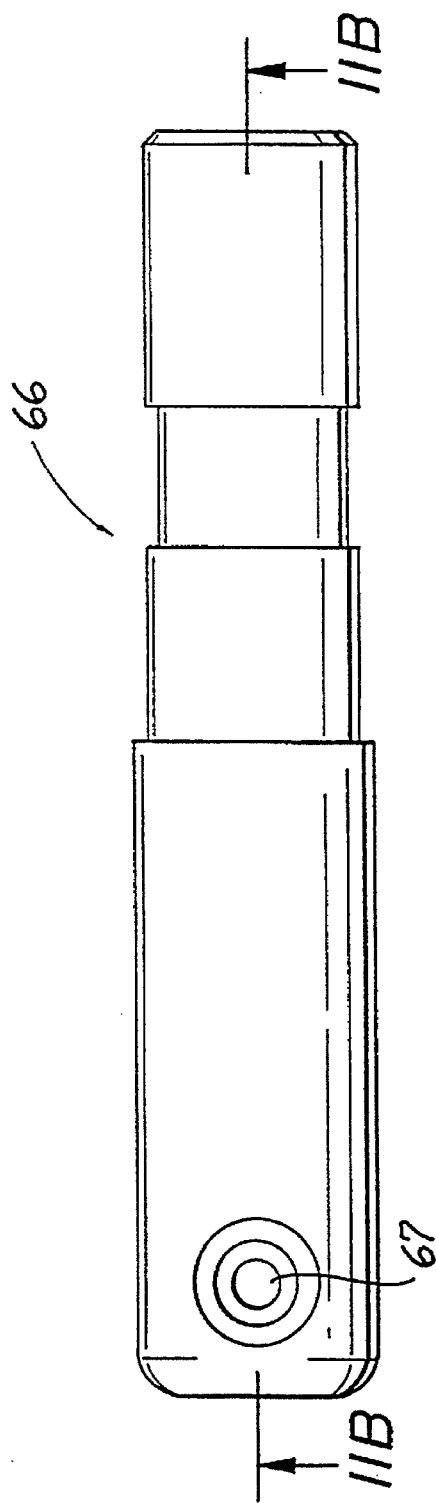
FIG. 11A illustrates a side view of a housing member of an endoscopic surgical instrument according to the present invention.
Figure 11B:
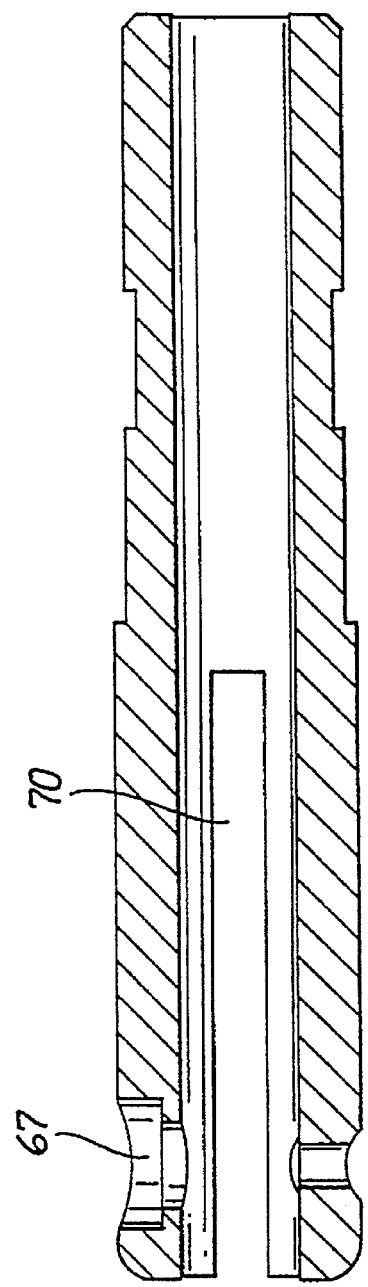
FIG. 11B illustrates a top cutaway view along lines A—A of FIG. 11A of a housing member of an endoscopic surgical instrument according to the present invention.

FIGS. 6A and 6B illustrate the tool mechanism which consists of, for example, a scissor mechanism including scissor blades 72 and 74. In this embodiment, a housing member 66 is attached to outer tube 20, and the tool mechanism is attached to housing member 66. Housing member 66 is shown in detail in FIGS. 11A and 11B, in which a radial hole 67 is provided to accept pivot pin 68 to allow the tool mechanism to pivot about pin 68 during opening and closing. Housing member 66 is provided with a longitudinal slot 70 which allows the jaw members which comprise the tool mechanism to open and close, as best seen in FIGS. 11A and 11B.

As also shown in FIG. 6A, stiffening members 75 may be provided on scissor blades 72 and 74 which reinforce the blades and add strength to the blades. Stiffening members 75 allow for a very thin construction for blades 72 and 74, particularly at the distal end 77. Stiffening members 75 may comprise a detent or outwardly punched region whose addition to blades 72 and 74 bias the blades towards each other to enhance the shearing function of the blades. As the blades are made thinner, the resiliency of the blade material, preferably stainless steel, titanium, or a like metal, tends to decrease, and the provision of stiffening members 75 urges the blades 72 and 74 toward each other to maintain the efficiency of the cutting action. It is also contemplated that stiffening members 75 may comprise a built up region of material, or a layer of material fastened to the blades by adhesives, solder, or the like.

As best seen in FIG. 6B, scissor blades 72 and 74 are shown in the open position whereby the handle members (not shown) are in the open position, i.e., pivoting handle 16 is moved away from stationary handle 14.

As the handles move, inner rod member 22 slides through outer tube 20 towards jaw mechanism 28. As seen in FIG. 6B, scissor blades 72 and 74 are provided with cam slots 76 and 78, which slots accept a bearing post 80 which is attached to inner rod 22. As rod 22 moves, bearing post 80 slides within cam slots 76 and 78 to pivot blades 72 and 74 about stationary pivot pin 68 to open and close the blades. When the blades open, the tail end of the blades pass through slot 70 in housing member 66 to allow the blades to open.

When handle members 14 and 16 are drawn toward each other, inner rod 22 slides away from the jaw mechanism and draws bearing post 80 towards the handle assembly. As this occurs, bearing post 80 slides in cam slots 76 and 78 to draw the blades closed.

Figure 7:
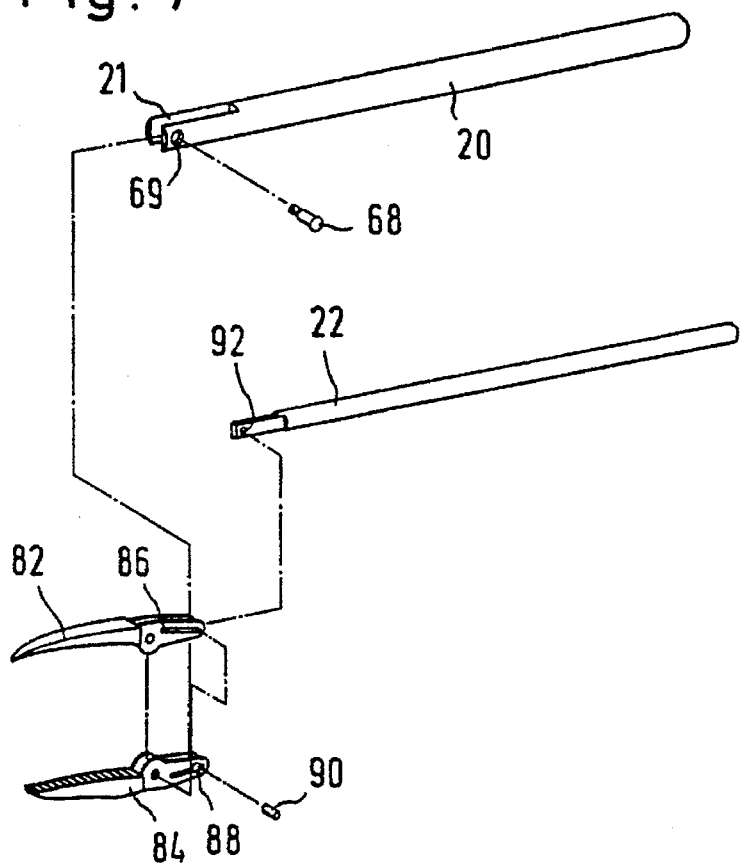
FIG. 7 illustrates an exploded perspective view of an alternate tool mechanism of an endoscopic surgical instrument according to the present invention.

Turning to FIG. 7, FIG. 7 illustrates an exploded perspective view of a dissector device which may comprise tool mechanism 28. In this embodiment, outer tube 20 is provided with a slot 21 which allows for the opening and closing of the dissector members. In this embodiment, housing member 66 is eliminated.

The dissector members 82 and 84 are provided with a cam slot arrangement similar to the device illustrated in FIG. 6B. Cam slot 86 is provided on upper dissector member 82, and cam slot 88 is provided on lower dissector member 84. In this embodiment, inner rod 22 is positioned within outer tube 20, while dissector members 82 and 84 are pivotably secured to outer tube 20 by means of pivot pin 68 which passes through hole 69 in tube 20. Rod 22 is secured to the cam slot arrangement through the provision of bearing post member 90. As rod member 22 is slid forward within tube 20, bearing post 90 slides in cam slots 86 and 88 to pivot the dissector members about pivot point 68 to open the members, and when the rod member 22 is slid away from the dissector mechanism, post 90 slides in cam slots 86 and 88 away from the dissector mechanism to draw the dissector members 82 and 84 into a closed position, as best seen in FIG. 9.

Figure 9:
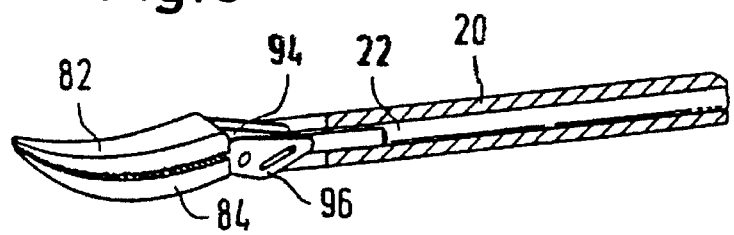
FIG. 9 illustrates a partial cutaway side view of the dissector mechanism of FIGS. 8A and 8B attached to the end of an endoscopic surgical instrument according to the present invention.

As also seen in FIG. 9, as the jaws close, the distal tips of the jaw members 82 and 84 contact each other before the ends nearest the pivot point contact each other. An angle of less than 6° is maintained at this point, and preferably 2°, to allow for progressive application of pressure at the jaws.

Figure 8A:
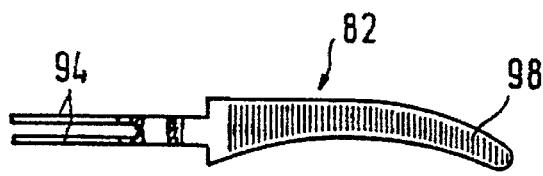
FIG. 8A illustrates a plan view of the upper member of a dissector mechanism for use with an endoscopic surgical instrument according to the present invention.
Figure 8B:
FIG. 8B illustrates a plan view of a bottom member of a dissector mechanism for use with an endoscopic surgical instrument according to the present invention.

FIGS. 8A and 8B illustrate the preferred embodiment of the dissector device, in which the body portion has a crescent shape to facilitate grasping and tearing tissue. The surface of the dissector members include serrations 98 which are provided for dissecting and tearing tissue during a surgical procedure. Overlapping projections 94 and 96, on which cam slots 86 and 88 are formed, allow the dissector mechanism to open and close without interfering with each other. The spacing between projections 94 is less than the spacing between projections 96, such that projections 94 fit within projections 96. Slot 21 is provided on outer tube 20 allow the projections to pass outside the perimeter of tube 20 to allow the dissector mechanism to open and close.

Figure 10A:
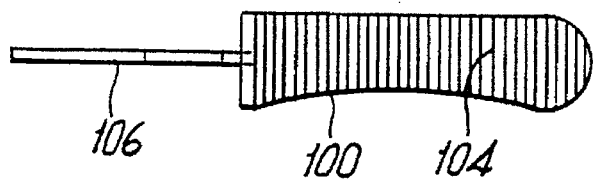
FIG. 10A illustrates a plan view of an upper member of a molded plastic grasper mechanism.
Figure 10B:
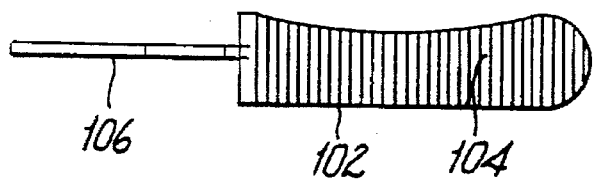
FIG. 10B illustrates a plan view of a bottom member of a molded plastic grasper mechanism.
Figure 10C:
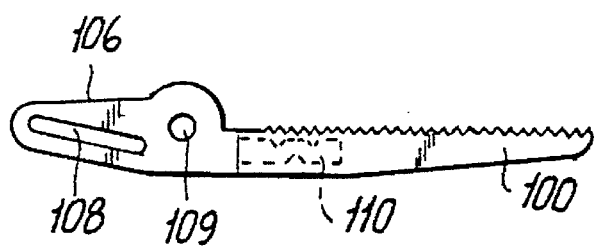
FIG. 10C illustrates a side view of a member of a grasper mechanism.

FIGS. 10A through 10E illustrate a grasping mechanism which may be used as the tool mechanism on the endoscopic surgical instrument of the present invention. FIGS. 10A and 10B illustrate a cooperating pair of grasping members 100 and 102 which are provided with serrations 104 to facilitate the grasping and holding of tissue. In the embodiment shown in FIGS. 10A and 10B, the body portions 100 and 102 are preferably constructed of a plastic material which is integrally molded about projection 106. As best seen in FIG. 10C, a post member 110 is provided about which the members 100 and 102 are molded. Projection 106 is provided with cam slot 108 and pivot hole 109 so that the grasping mechanism may be operated in a manner similar to that previously described above in connection with the scissor mechanism and the dissector mechanism.

Figure 10D:
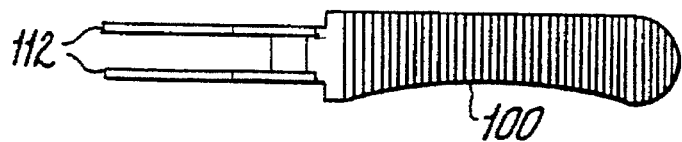
FIG. 10D illustrates a plan view of an upper grasper member constructed of metal.
Figure 10E:
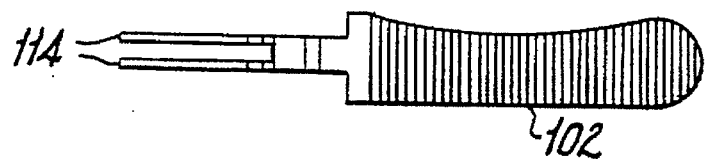
FIG. 10E illustrates a plan view of a bottom member of a grasper mechanism constructed of metal.

FIGS. 10D and 10E illustrate the grasping mechanism of FIGS. 10A through 10C except where the entire mechanism is constructed of metal, such as stainless steel, titanium, cast aluminum or the like. Projections 112 and 114 cooperate in a manner similar to that described above for the dissector device, where projections 112 are spaced greater than the distance between the projections 114 so that projections 114 may pass between projections 112 during opening and closing of the grasping device.

Figure 12A:
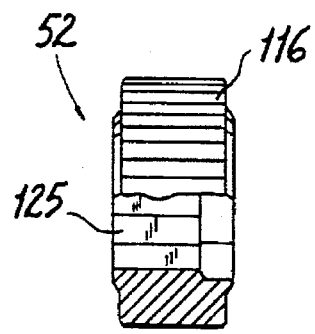
FIG. 12A illustrates a side partial cutaway view of a rotator knob for use in an endoscopic surgical instrument of the present invention.
Figure 12B:
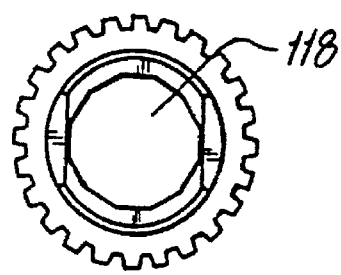
FIG. 12B illustrates a front view of the rotatable knob of FIG. 12A.
Figure 13A:
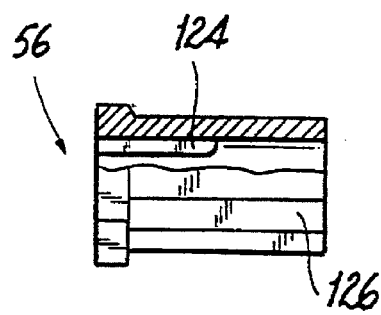
FIG. 13A illustrates a side partial cutaway view of a bushing member for use in an endoscopic surgical instrument according to the present invention.
Figure 13B:
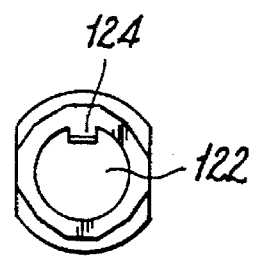
FIG. 13B illustrates a front view of the bushing of FIG. 13A.

Turning now to FIGS. 12 and 13, there is illustrated the rotatable knob 52 and bushing member 56 which are used in connection with the rotatable body portion to rotate the body portion and tool mechanism. Rotatable knob 52 is preferably knurled or provided with ridges 116 to allow for easy manipulation by the surgeon's thumb or fingers. Rotatable knob 52 is preferably hollow and includes a passageway 118 to allow the bushing member 56 to pass therethrough. FIG. 13A illustrates the bushing member as having a polygonal cross-section, such that it is provided with a series of faces 126 which cooperate with faces 125 on the rotatable bushing. The bushing extends outwardly from rotatable knob 52 (see FIG. 4), and faces 126 cooperate with boss structure 57 (see FIG. 5) to provide for incremental rotation of the body portion 18 to position the tool mechanism at various points along the rotational axis. FIG. 13B best illustrates boss member 124 which allows for connection and securement of the bushing to outer tube 20. Boss 124 fits into a groove or slot in tube 20 to secure the bushing and rotatable knob to outer tube 20. It is also contemplated that bushing 56 and rotatable knob 52 are constructed as a single integral unit. Knob 52 and bushing 56 are preferably constructed of plastic, so that insulation is provided during use of the electrocautery feature.

The positioning of the rotatable knob on the stationary handle allows the surgeon to use the endoscopic surgical instrument 10B with one hand, so that as the surgeon is holding the device he may rotate the knob with his thumb while keeping his other hand free to control the surgical procedure.

Figure 14A:
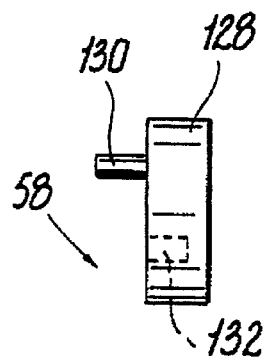
FIG. 14A illustrates a side view of a pivot bushing for use with an endoscopic surgical instrument according to the present invention.
Figure 14B:
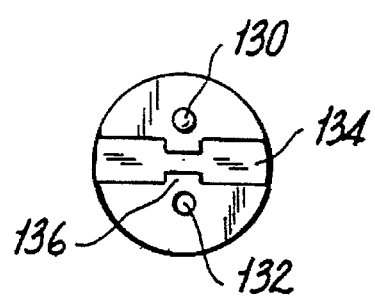
FIG. 14B illustrates a front view of the pivot bushing of FIG. 14A.

As the knob is rotated, the outer tube is rotated which in turn rotates pivot point 68, which consequently rotates the tool mechanism. Rotation of the tool mechanism causes rotation of the inner rod 22, which is accomplished within pivot bushing 58. Pivot bushing 58 is best illustrated in FIGS. 14A and 14B and comprises a pair of discs 128 each having a post member 130 and a hole 132 formed therein for interengaging the discs with each other. Groove 134 is provided with a notch portion 136 which accepts the end of rod member 22 which is formed with a corresponding notch. This notch secures rod 22 in place for longitudinal movement, while at the same time allowing for rotational movement. As stated above, as handle member 16 pivots, bushing 58 rotates to greatly reduce or eliminate radial deflection of the rod member within the tube. This alleviates the torquing forces on the rod and minimizes damage to the device after extended use.

Figure 15A:
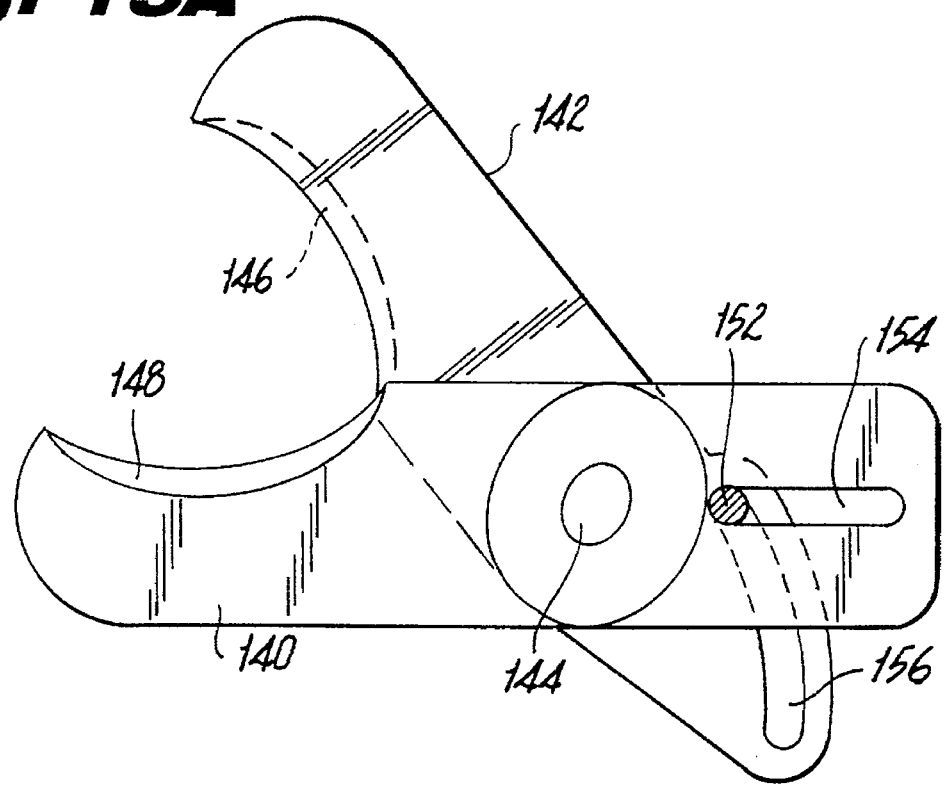
FIG. 15A illustrates a side view of an open scissor mechanism in accordance with the present invention wherein only one jaw member pivots.
Figure 15B:
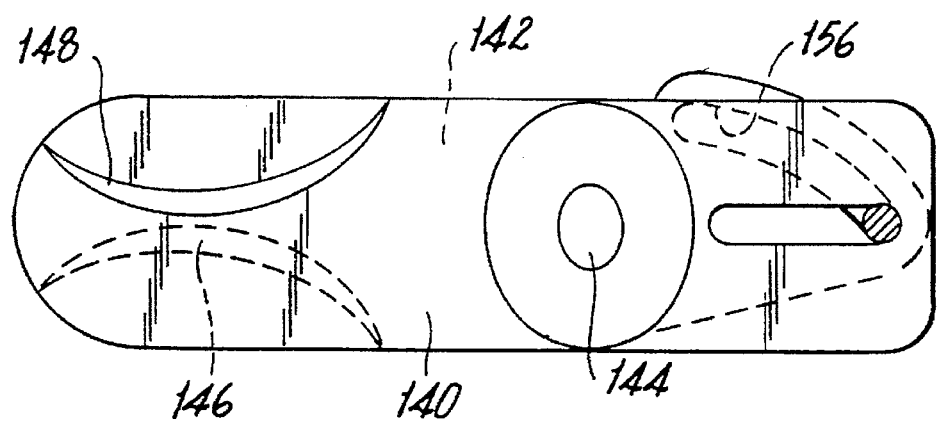
FIG. 15B illustrates a side view of the scissor mechanism of FIG. 15A in the closed position.

FIGS. 15A and 15B illustrate a further embodiment of the tool mechanism in accordance with the present invention.

Figure 15C:
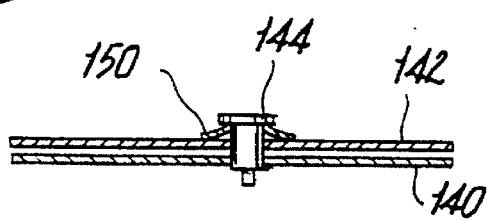
FIG. 15C illustrates a top view in cross-section of the stationary pivot pin of the scissors in FIGS. 15A and 15B.

Stationary scissors blade 140 is attached to movable scissors blade 142 about transverse stationary pivot pin 144. This transverse pin 144 is attached to housing member 66 through radial hole 67 as discussed above (see FIGS. 11A and 11B). The present scissors embodiment utilizes a shearing motion of blades 140 and 142 in order to separate tissue. Arcuate cutting surfaces, 146 and 148 respectively, are formed on opposed vertical faces of the distal ends of blades 140 and 142 to better facilitate the shearing cutting action. In a particularly advantageous embodiment, a spring washer 150, see FIG. 15C, is provided to urge movable blade 142 against stationary blade 140. The urging force providing a better cutting action as the blades 140 and 142 shear against each other.

A transverse bearing post 152 is attached to inner rod 22 and adapted for reciprocal longitudinal motion within outer tube 20. A longitudinal slot 154 is provided in a proximal end of stationary blade 140 in an area proximal to and in longitudinal alignment with transverse pivot pin 144. Bearing post 152 interfits with slot 154 for longitudinal motion therein and serves to prevent pivotal motion of blade 140 about pivot pin 144.

An arcuate cam slot 156 is provided in a proximal end of movable blade 142 in an area proximal to transverse pivot pin 144. Bearing post 152 interfits within arcuate cam slot 156 and serves to translate the longitudinal motion of inner rod 22 relative to outer tube 20 into pivotal motion of blade 142 about pivot pin 144. Thus, in the embodiment shown in FIGS. 15A and 15B, as transverse bear post 152 moves distally from its proximal position, blade 142 is cammed open relative to blade 140 which remains in the same longitudinal plane as rod 22. Correspondingly, proximal motion of rod 22 causes bear post 152 to cam blade 142 to a closed position as shown in FIG. 15B.

This embodiment is directed to a shearing scissors mechanism, however, other mechanisms such as, for example, graspers, dissectors, clamps etc. are contemplated.

FIGS. 16 through 21 illustrate additional unique embodiments of grasping mechanisms which may be used as tool mechanisms on the endoscopic surgical instrument described above. These embodiments are particularly suited for grasping and securely holding a gallbladder or other similarly sized piece of tissue or organ as it is repositioned within or removed from a body through a cannula or the like. The handle assembly 12 and body portion 18 of these embodiments may be the same as previously described with regard to other embodiments. These embodiments of the instrument may include a housing member 66 or, alternatively, the housing member 66 may be eliminated, as described earlier in connection with other embodiments.

Figure 16:
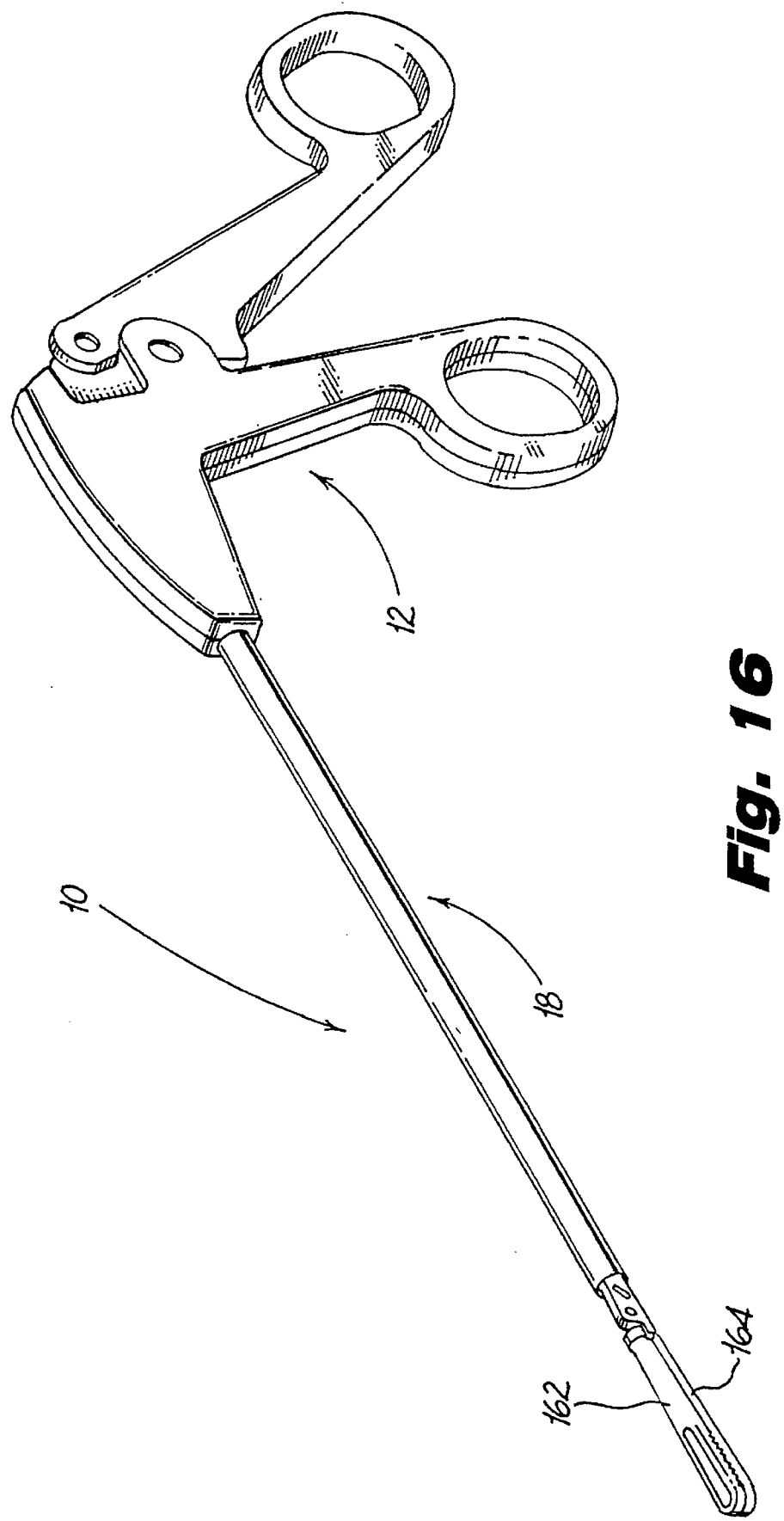
FIG. 16 illustrates a perspective view of an alternate embodiment of an endoscopic surgical instrument in accordance with the present invention.
Figure 17:
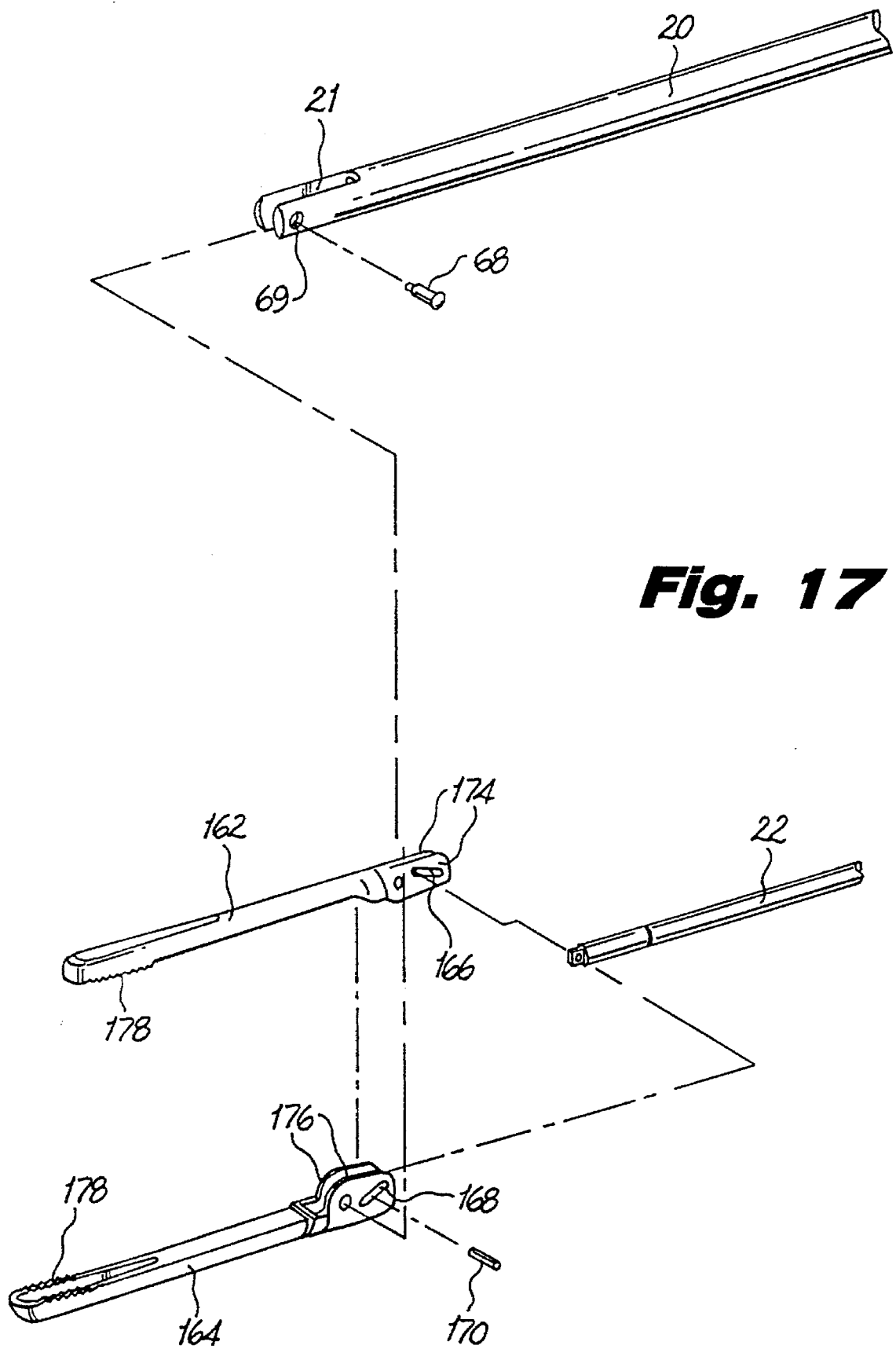
FIG. 17 illustrates an exploded perspective view of the grasper mechanism of FIG. 16.

In the embodiment of FIG. 16, the grasping jaws 162, 164 are elongated to provide a relatively wide opening when the jaws are separated, thus facilitating passage of a gallbladder or similar tissue therebetween for grasping.

The grasping jaws 162 and 164 are provided with a cam slot arrangement on a proximal end thereof similar to the devices previously illustrated. Cam slots 166 and 168 are provided on upper grasping jaw 162, and lower grasping jaw 164, respectively. Inner rod 22 is positioned within outer tube 20, while grasping jaws 162 and 164 are pivotably secured to the distal end of outer tube 20 by means of pivot pin 68 which passes through hole 69 in tube 20. Rod 22 is secured at the distal end to the cam slot arrangement through the provision of bearing post member 170. As rod member 22 slides forward within tube 20, bearing post 170 moves in cam slots 166 and 168 to pivot the grasping jaws about pivot point 68 to open the jaws. The reverse motion draws the grasping jaws 162 and 164 into a closed position. The included angle formed by cam slots 166 and 168 when the instrument is assembled is preferably between about 60 and about 80° to provide an appropriately wide opening between the jaws when separated, yet reducing or minimizing the distance which the projections 174 and 176 extend beyond the shaft when the jaws are fully opened.

As the jaws close, the distal tips of the jaw members 162 and 164 preferably contact each other before the ends nearest the pivot point contact each other. An angle of less than about 6° and preferably about 2°, is maintained at the point of initial contact to allow for progressive application of pressure at the jaws.

Figure 18A:
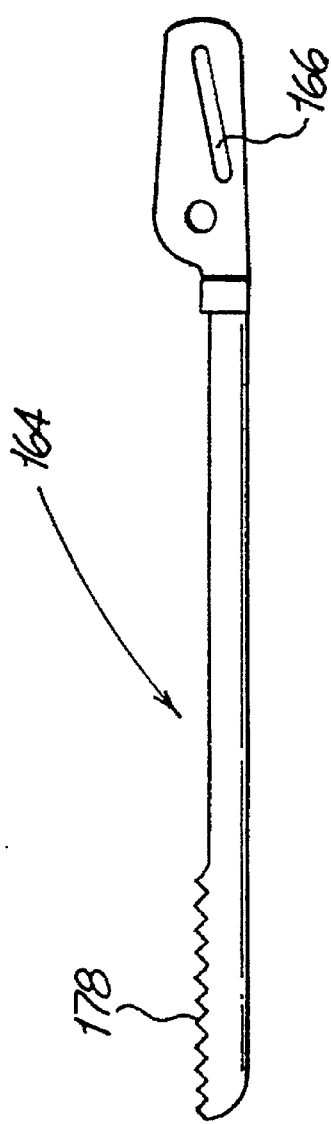
FIGS. 18A and 18B illustrate a side and plan view, respectively, of the lower grasper member of the embodiment shown in FIG. 16.
Figure 18B:
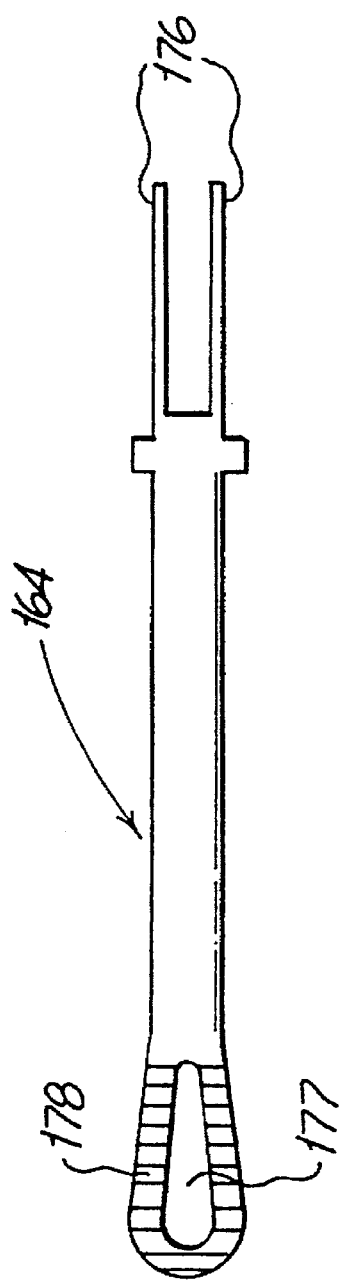

As best seen in FIGS. 18A and 18B, each jaw flares in a transverse direction at its distal end to facilitate grasping and holding tissue. The inner facing surfaces of the distal ends of grasper jaws 162, 164 include serrations 178 for securely grasping tissue during a surgical procedure. Opening 177 is provided in each grasper member 162, 164 to allow a portion of the tissue being grasped to protrude through the jaws, if necessary, to further facilitate atraumatic grasping and holding of the tissue. Opening 177 also allows fluid within the tissue structure, e.g., gallbladder to exude therefrom as it is being repositioned within or removed from the abdomen through the cannula. While shown as a single, elongate opening along the longitudinal axis of the jaw members, one of ordinary skill in the art will appreciate that one or more openings of any shape may be provided to allow fluid removal and/or accommodate tissue.

Projections 174 and 176 cooperate in a manner similar to that described with respect to the previously described grasper and dissector devices, that is, projections 176 are spaced greater than the distance between projections 174 so that projections 174 may pass between projections 176 during opening and closing of the grasping device.

Stabilizing means such as a torsion spring (not shown) may be used to remove any torsional play or wobble which might be encountered in the elongated jaw members.

FIGS. 19A to 21 show another embodiment of a grasper mechanism particularly suited for grasping and securely holding tissue or organs as they are removed from a body through a cannula or the like. The grasping jaws 182, 184 of this embodiment employ rounded teeth 198 to minimize trauma to the tissue being removed.

Figure 19A:
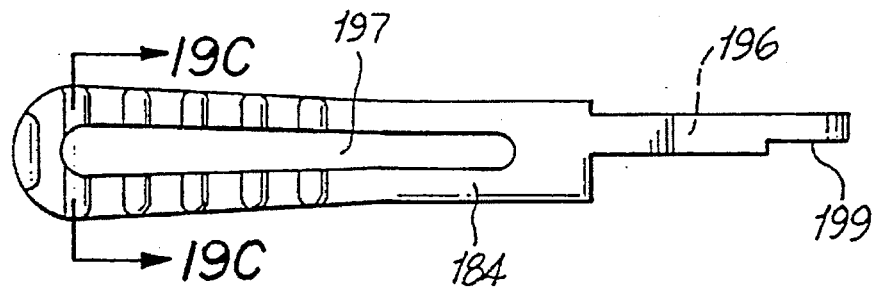
FIGS. 19A and 19B illustrate plan and side views, respectively, of the jaw member of another embodiment of a grasper mechanism in accordance with the present invention.
Figure 21:
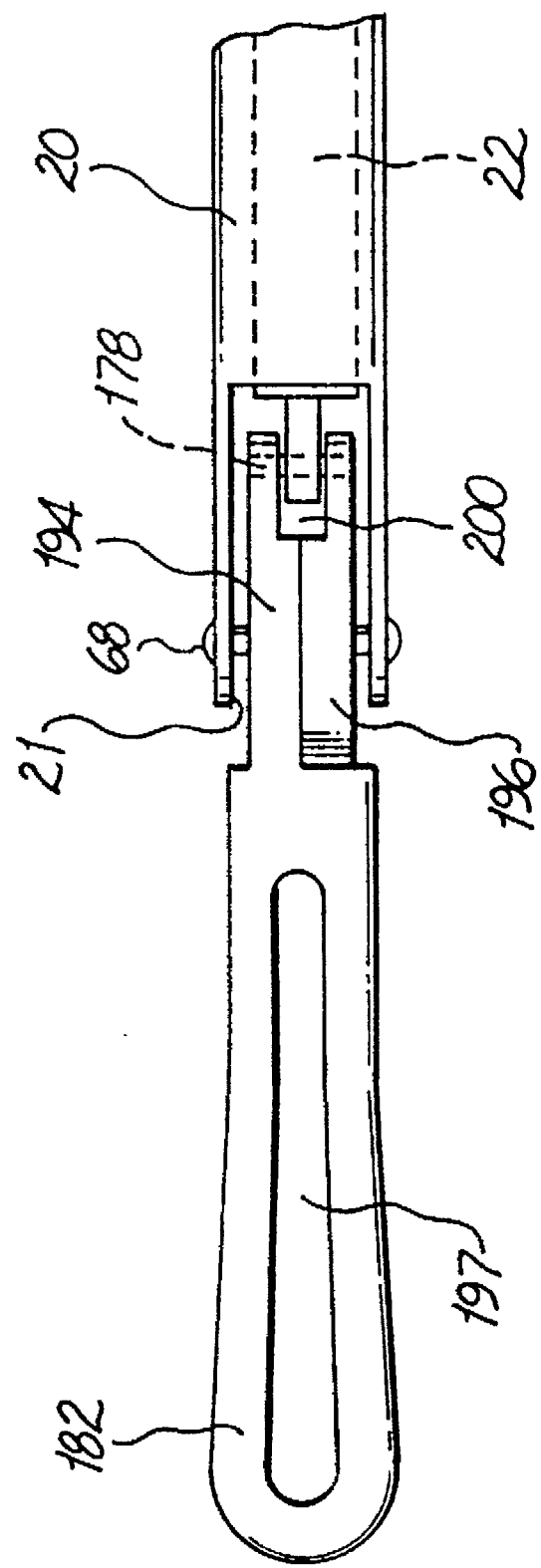
FIG. 21 illustrates a plan view of the grasper mechanism shown in FIG. 20.
Figure 22:
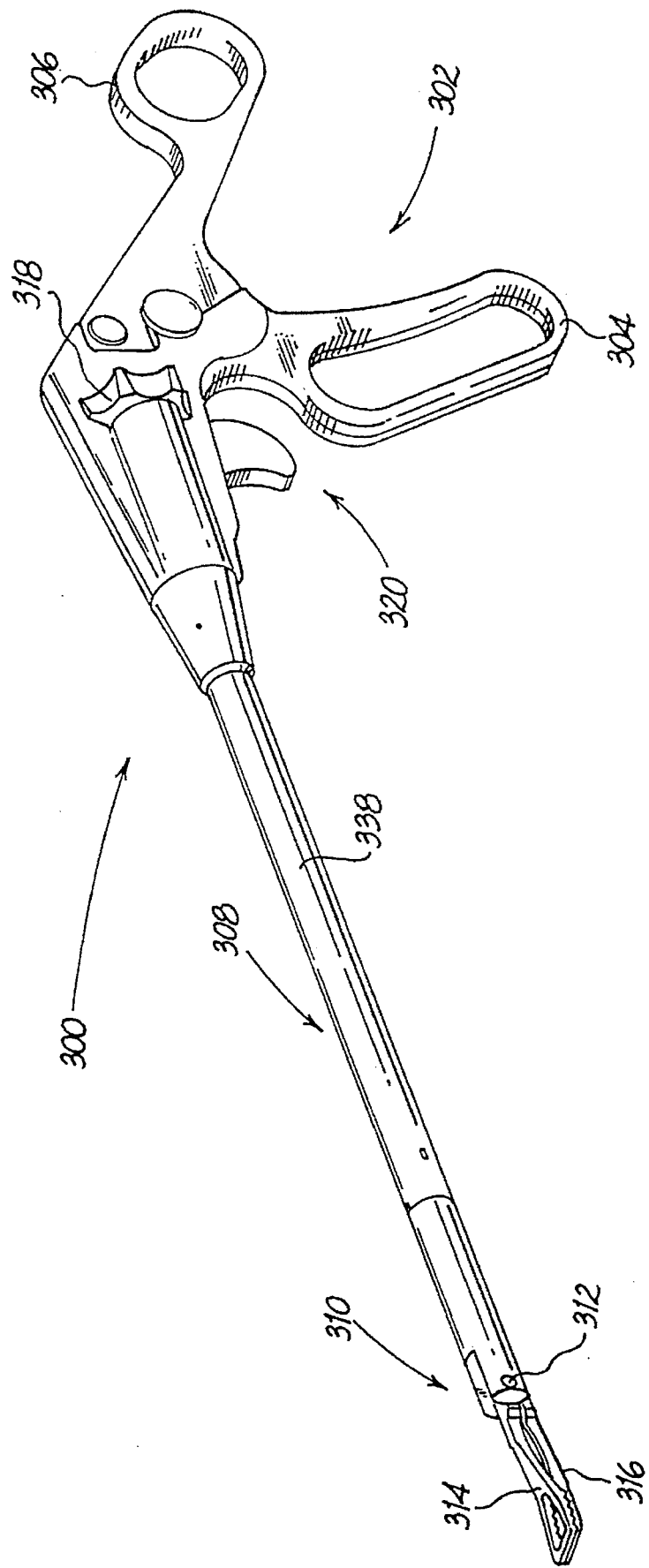
FIG. 22 illustrates a perspective view of an endoscopic surgical instrument employing a grasping tool mechanism for grasping and holding lung tissue in accordance with the present invention.

The grasping jaws 182 and 184 are provided with a cam slot arrangement similar to the devices previously illustrated with the exception that grasping jaws 182, 184 each have only one projection 194, 196, respectively on which cam slots 186 and 188 are formed. Additionally, as best seen in FIGS. 19A and 21, a recess 199 may be formed in each projection 194, 196 which will cooperate when the jaws are assembled to form slot 200 to receive the end of rod 22.

Figure 19B:
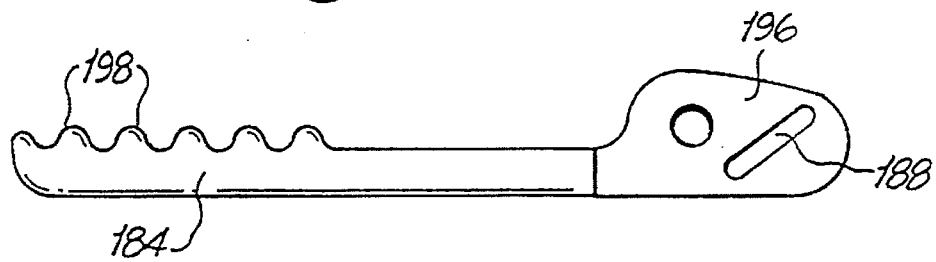
Figure 19C:
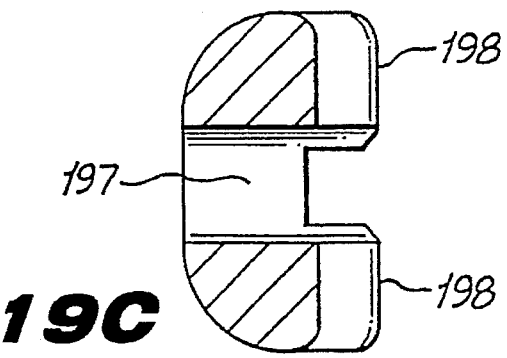
FIG. 19C illustrates a cross-section view along section A—A of FIG. 19A.
Figure 20:
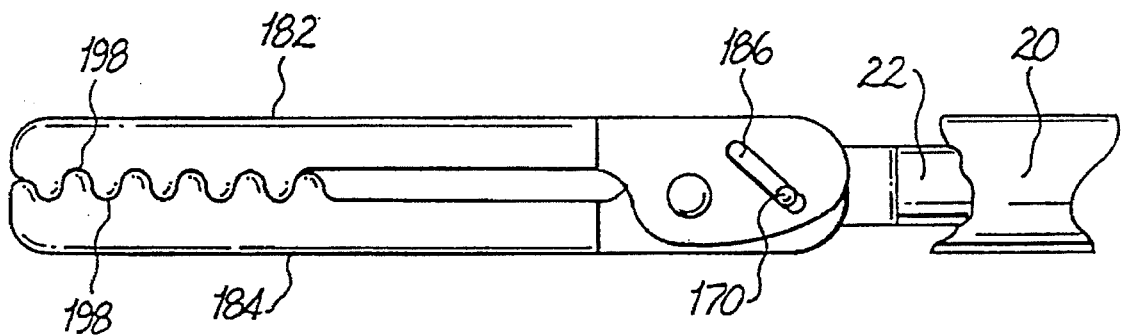
FIG. 20 illustrates a side view of the grasper mechanism in accordance with the embodiment shown in FIGS. 19A–C.

Referring to FIGS. 19B and 20, the inner surfaces of grasping jaws 182 and 184 are provided with interdigitating, rounded teeth 198. For most purposes, the angles of the teeth and corresponding grooves or valleys between the teeth will be equal along the length of the jaw. The pitch of the sides of the teeth 198 may advantageously range between about 10° and about 45° from an imaginary line normal to the gripping surface of the grasping jaw and passing through the apex of the tooth. Preferably, the pitch of the teeth ranges from about 25° to about 35° to provide maximum gripping strength.

The teeth 198 in the embodiment of FIGS. 19A–21 are rounded to prevent trauma to the tissue being gripped. The teeth on grasping jaw 182 are offset from the teeth on grasping jaw 184 and the valleys between the teeth are also rounded. Thus the teeth on the grasping jaws 182, 184 will mesh and directly interfit when the jaws are in the closed position as best seen in FIG. 20. At least one tooth may advantageously be located distally from opening 197 formed in grasping jaws 182 and 184 to facilitate gripping at the tip of the jaws.

The corners and edges of the grasping members 182 and 184 may also be rounded to prevent damage to the tissue being gripped or surrounding tissue.

Opening 197 is provided in grasping members 182 and 184 to allow tissue or fluid to pass through the jaw members, if necessary, to further facilitate atraumatic grasping and secure holding of the tissue.

Turning now to FIGS. 22–25, there is illustrated an endoscopic lung clamp instrument which facilitates the grasping and holding of lung tissue during an endoscopic surgical procedure. Instrument 300 essentially comprises a handle assembly 302 which includes a stationary handle 304 and a movable handle 306. However, it is contemplated that both handles 304 and 306 may be movable if desired. Secured to handle assembly 302 is a body assembly 308 which includes an outer tube 338 through which an inner rod member (not shown) reciprocatingly slides in response to movement of movable handle 306. Body assembly 308 is similar to that described above in reference to FIGS. 1–21. Body assembly 308 terminates in tool mechanism 310.

Handle assembly 302 further includes a rotatable knob 318 for rotating body assembly 308 to orient the tool mechanism 310 at a particular position. A ratchet mechanism 320 may also be provided for incrementally opening and closing the handle assembly 302 and consequently the tool mechanism 310. Several types of ratchet mechanisms 320 and handle assemblies 302 are disclosed in application Ser. No. 196,886, filed Feb. 15, 1994, now. U.S. Pat. No. 5,483,952, issued Jan. 16, 1996, which is a continuation of U.S. application Ser. No. 765,993, filed Sep. 26, 1991, now abandoned. One specific type of such ratchet mechanisms will be described hereinbelow with reference to FIGS. 26–29.

Referring to FIGS. 26–29, an endoscopic surgical instrument which incorporates a ratchet mechanism as disclosed in U.S. application Ser. No. 196,886, filed Feb. 15, 1994, and U.S. Pat. No. 5,483,952 is illustrated. For convenience of illustration, the instrument incorporating such ratchet mechanism will be described utilizing series "400" numerals. Instrument 400 is similar to the instruments previously described, and includes a handle assembly 402, a housing assembly 410, and a ratchet mechanism 420. Handle assembly 402 includes a pivoting handle 404, a stationary handle 406, and a barrel portion 408, to which body assembly 410 is secured. Body assembly 410 includes an outer tubular member 412 and a coaxial inner rod member 414 which slides therein. Outer tubular member 412 is secured to barrel portion 408, while inner rod member 414 is secured to pivoting handle 404 and reciprocates within outer tubular member 412 upon movement of pivoting handle 404. A rotation knob 416 is provided to adjust the orientation of the tool mechanism shown in FIGS. 16–21, which is located at the distal end of the body assembly 410. Ratchet mechanism 418 is provided, along with actuation means 420, the function of which will be described below.

Figure 26:
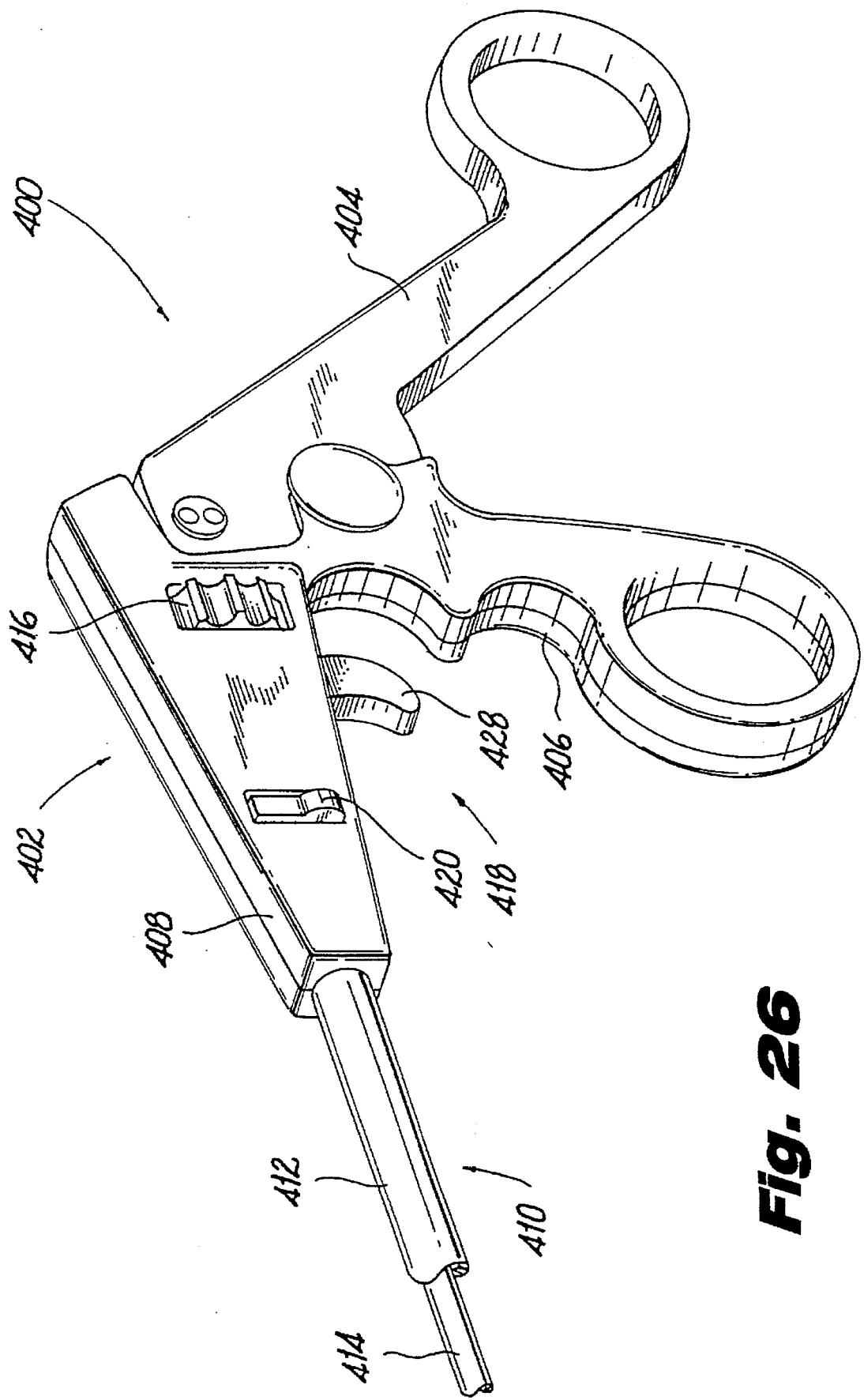
FIG. 26 illustrates an embodiment of the endoscopic surgical instrument which incorporates a ratchet mechanism.
Figure 27:
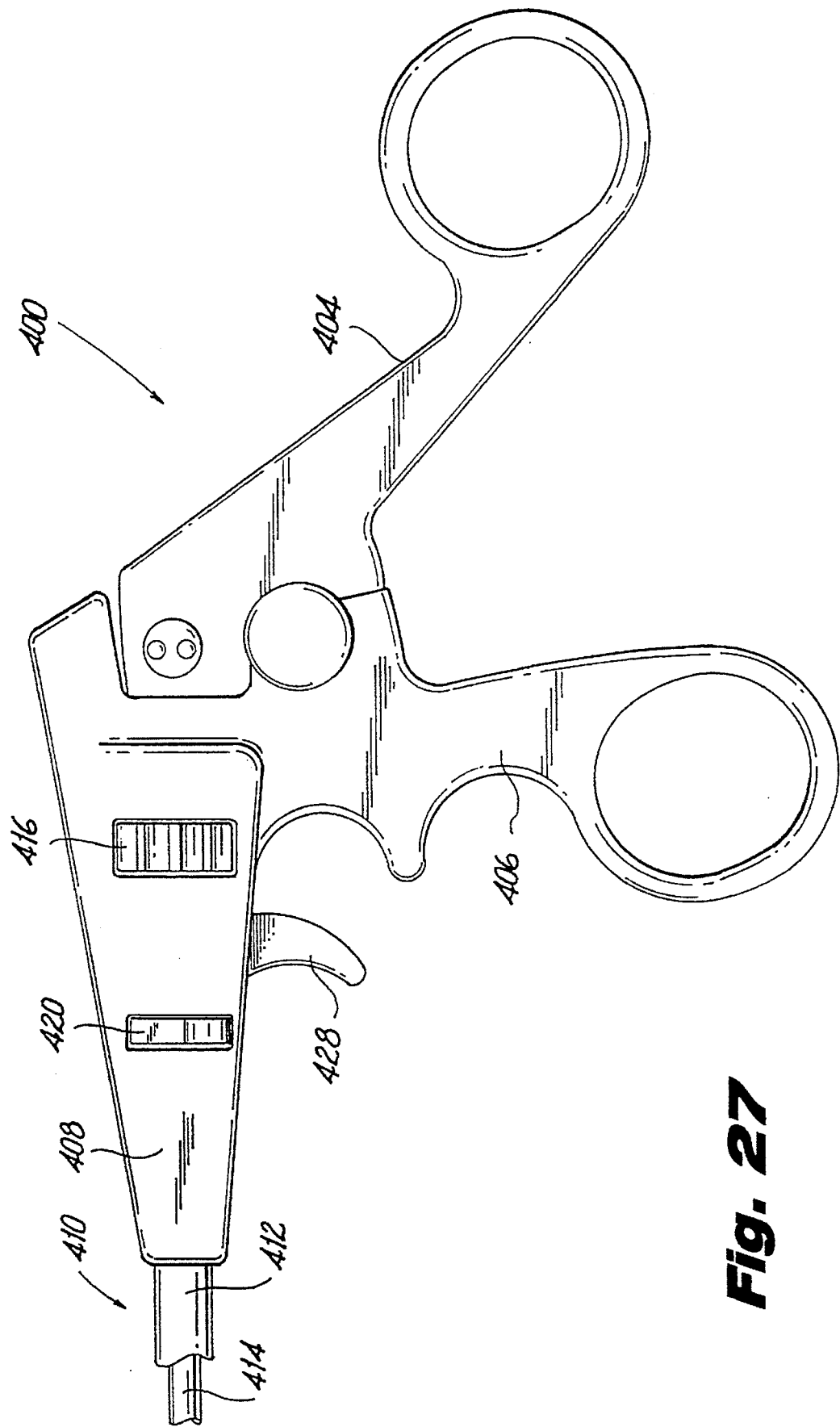
FIG. 27 illustrates a side plan view of the device of FIG. 26.

Referring specifically to FIG. 28 in conjunction with FIGS. 26 and 27, the ratchet mechanism 418 is illustrated. Inner rod member 414 includes a rack member 442 which includes a plurality of circumferential notches or indentations which allows for use of the ratchet mechanism 418 regardless of the orientation of the tool mechanism due to rotation of housing assembly 410 by rotation knob 416. Ratchet mechanism 420 includes an articulated body which is formed by pawl member 424, trigger member 428 and a camming member 434 which extends from pawl member 424. Trigger member 428 pivots about a stationary pivot point 431 and is biased in the forward direction by spring 426. Trigger member 428 is joined to pawl member 424 through floating pivot point 430, while pawl member 424 is pivoted further about stationary pivot point 432.

Actuation means 420 is provided, which is best seen in FIG. 29. Actuation means 420 comprises a body portion 486 and is provided with a camming slot 436 into which camming member 434 passes as best shown in FIG. 28. Camming surface 438 engages camming member 434 to urge pawl member 424 into engagement with rack member 422. When actuation means 420 is pushed in a first direction, camming member 434 disengages from camming surface and pawl member 424 disengages from rack member 422. When actuation means 420 is pushed in the opposite direction, camming surface 438 contacts camming member 434 which urges pawl member 424 into engagement with rack member 422. Actuation means 420 functions as a switch to the user to override the ratchet mechanism so that the instrument may be used in a conventional manner without requiring the user to hold any component of the instrument.

Referring once again to FIGS. 22–25b, tool mechanism 310 comprises a lung grasping or clamping mechanism for gripping and securing holding soft and delicate tissue such as lung tissue. Tool mechanism 310 essentially comprises a pair of reciprocatingly movable jaw members including first jaw member 314 and second jaw member 316. Tool mechanism 310 is secured to body assembly 308 by pivot pin 312 in a manner described above.

Figure 23:
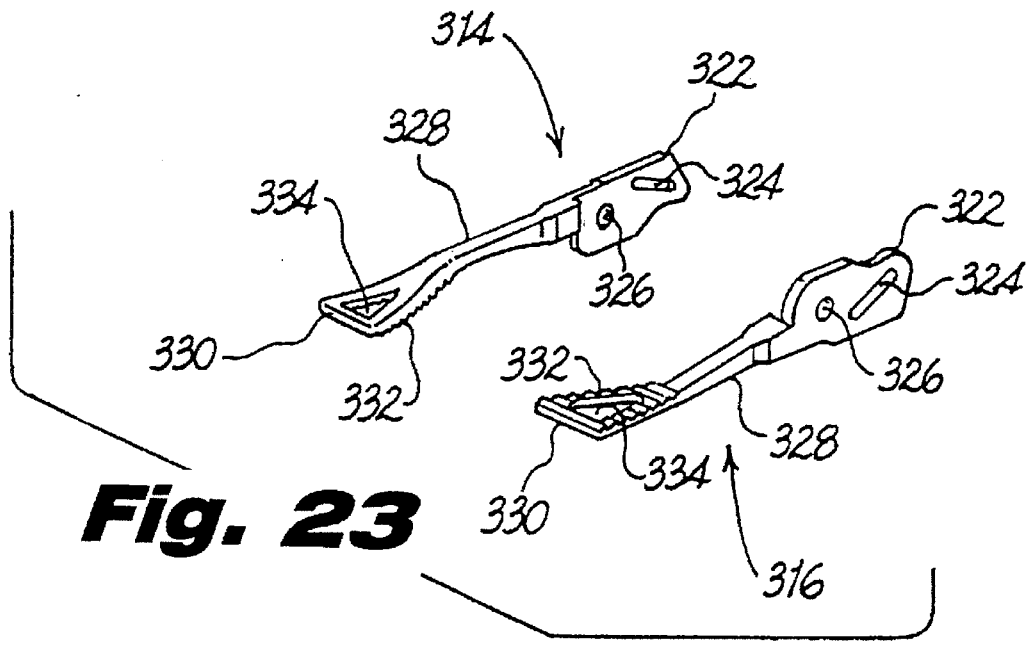
FIG. 23 illustrates an exploded perspective view of the grasping tool mechanism of FIG. 22.

In order to facilitate the grasping and holding of delicate tissue such as lung tissue, jaw members 314 and 316 have a widened triangular gripping portion 330, which preferably has a width between 10 and 12 millimeters. Each jaw member includes a camming portion 322 which includes a cam slot 324 and a pivot hole 326 which accommodates pivot pin 312. It is best seen in FIG. 23, pivot holes 326 are in alignment and cam slots 324 overlap each other and cooperate with a linkage mechanism which is secured to the inner rod member of body assembly 308 and in which operates in a manner such as that described above in reference to FIGS. 1–21. Camming portion 322 extends into gripping portion 330 through a transition body portion 328.

Figure 24:
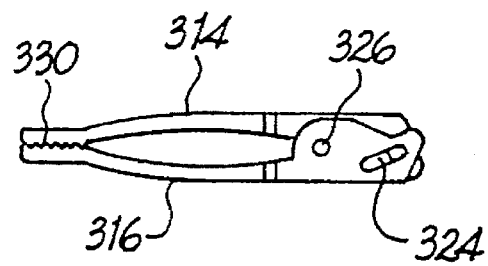
FIG. 24 illustrates a side plan view of the grasping tool mechanism of FIG. 22.
Figure 25A:
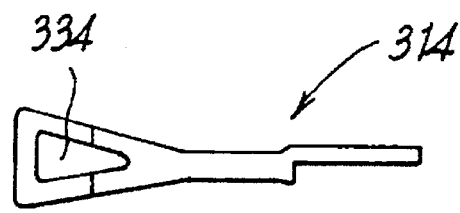
FIGS. 25a and 25b illustrate a top plan view of the upper grasping member and a top plan view of the lower grasping member, respectively, of the grasping tool mechanism of FIG. 22.
Figure 25B:
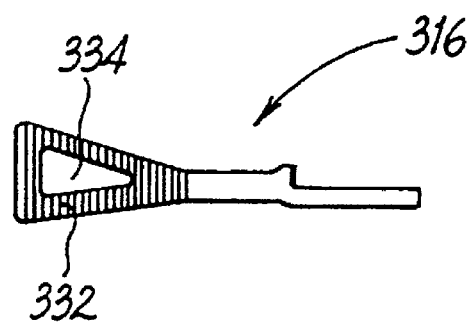

Gripping portion 330 has a substantially triangular shape to provide a greater surface area for gripping delicate tissue such as lung tissue. As is best seen in FIG. 25, each jaw member 314 and 316 includes a substantially triangular shaped opening which corresponds in shape to the triangular shape of the gripping portion. Opening 334 allows the soft tissue to pass through the jaw member to prevent damage to the tissue and to further facilitate atraumatic grasping of the tissue. Openings 334 may be provided on one or both of the jaw members and serve to prevent crushing of the tissue between the jaw members and to facilitate grasping by receiving a portion of the tissue therein. Also facilitating the secure grasping of the tissue is the provision of a plurality of ribs 332 on each of the jaw members 314 and 316. As seen in FIGS. 23 and 24, the ribs meet and mesh at the gripping portion 330, and further extend partially along the length of the transition body portion 328 to further provide for gripping of the tissue. Ribs 332 may also abut against each other when the jaws close. Transition body portions 328 are offset from gripping portion 330 such that gripping portion 330 and transition body portion 328 are essentially parallel but in offset planes.

The endoscopic surgical instrument of the present invention is a compact, lightweight and easy to use instrument incorporating many features required during endoscopic surgical procedures which allows the surgeon to use the instrument with one hand thus freeing his other hand for other purposes during the surgery. The present instrument overcomes many of the disadvantages encountered with prior art devices and provides a precision instrument which is easy to handle and simple to manufacture. While the invention has been particularly shown and described with reference to the preferred embodiments, it will be understood by those skilled in the art that various modifications in form and detail may be made therein without departing from the scope and spirit of the invention. Accordingly, modifications such as those suggested above, but not limited thereto, are to be considered within the scope of the invention.

What is claimed is:

1. An endoscopic surgical instrument comprising:
   a handle assembly including a barrel portion, a stationary handle and a pivoting handle extending from said barrel portion, said barrel portion having an interior cavity accommodating at least a portion of said pivoting handle;
   a housing assembly extending distally from said handle assembly and defining a longitudinal axis, said housing assembly having a pair of coaxial members including an inner rod member reciprocatingly slidable longitudinally within an outer tube member in response to movement of said handle assembly;

a tissue gripping mechanism positioned at a distal end of said housing assembly pivotably secured to said outer tube member and operatively attached to said inner rod member, said tissue gripping mechanism including a pair of jaw members reciprocatingly movable between open and closed positions in response to movement of said inner rod member and said handle assembly;

wherein each of said jaw members of said gripping mechanism includes a camming portion attached to said inner rod member, a gripping portion at a distal end and a curved transition portion sloping with respect to said longitudinal axis between said camming portion and said gripping portion, said gripping portion tapering from said distal end towards said transition portion to form a triangular shaped portion having at least two substantially equal sides and said distal end forms a base of said triangular shaped portion perpendicular to said longitudinal axis, said triangular shaped portion having a corresponding triangular shaped central opening, and a plurality of parallel ribs extending transverse to said longitudinal axis for enhancing gripping of tissue therebetween, and wherein said curved transition portion is offset from said gripping portion such that said camming portion and said gripping portion are in substantially parallel planes when said jaw members are in said closed position; and a ratchet mechanism at least partially positioned within said interior cavity of said barrel portion of said handle assembly, said ratchet mechanism being operatively associated with at least one of said pair of coaxial members of said housing assembly to provide incremental movement of said tissue gripping mechanism.

2. An endoscopic surgical instrument according to claim 1, wherein said ribs contact each other when said jaw members are closed.

3. An endoscopic surgical instrument according to claim 1, wherein said ribs mesh adjacent each other when said jaw members are closed.

4. An endoscopic surgical instrument according to claim 1, wherein said handle mechanism includes a ratchet mechanism positioned within said handle mechanism, said ratchet mechanism engaging said inner rod member to provide for incremental positioning of said jaw members between open and closed positions.

5. An endoscopic instrument according to claim 1 wherein said camming portion includes a pivot aperture and a cam slot.

6. An endoscopic instrument according to claim 5 wherein said housing assembly extends in a first plane from said camming portion and said tissue gripping portion extends in a second plane from said housing assembly, said first plane and said second plane being substantially parallel.

7. An endoscopic surgical instrument having a handle mechanism including a barrel portion, a stationary handle and a pivoting handle extending from said barrel portion, said barrel portion having an interior cavity accommodating at least a portion of said pivoting handle, a housing assembly extending at a first end from said handle mechanism, said housing assembly defining a longitudinal axis and having a pair of coaxial members including an inner rod reciprocatingly slidable longitudinally in an outer tube in response to movement of said handle mechanism, and a jaw mechanism extending from said housing assembly at a second end and being movable between open and closed positions in response to movement of said inner rod, said jaw mechanism being pivotably secured to said outer tube and operatively attached to said inner rod, said jaw mechanism comprising a pair of tissue gripping members in opposed relation, said gripping members each including a proximal end which is operatively secured to said inner rod and positioned at said second end of said housing assembly, said gripping members each terminating in a distal end having a triangular shaped gripping portion, each gripping member further having a plurality of parallel ribs extending in a direction transverse to said longitudinal axis, and a triangular shaped opening generally central of said triangular shaped gripping portion, each gripping member further having a curved transition portion between said proximal end and said gripping portion, said transition portion sloping with respect to a plane defined by said longitudinal axis, such that said gripping portions contact each other at at least one location in said closed position while said transition portions remain spaced from each other, said gripping members further including means for enhancing gripping of tissue therebetween; and a ratchet mechanism at least partially positioned within said interior cavity of said barrel portion of said handle mechanism, said ratchet mechanism being operatively associated with at least one of said pair of coaxial members of said housing assembly to provide incremental movement of said pair of tissue gripping members.

8. An endoscopic instrument according to claim 7, wherein said gripping enhancing means comprises an opening in at least one of said tissue gripping members.

9. An endoscopic instrument according to claim 7, wherein said gripping enhancing means comprises a plurality of ribs, said ribs meshing adjacent each other when said jaw mechanism is closed.

10. An endoscopic instrument according to claim 7, wherein said gripping enhancing means comprises a plurality of ribs, said ribs abutting against each other when said jaw mechanism is closed.

11. An endoscopic instrument according to claim 7, wherein said gripping enhancing means comprises a triangular shaped opening in said tissue gripping members and a plurality of ribs surrounding said opening.

* * * * *